(12) United States Patent
Montagu et al.

(10) Patent No.: US 7,384,742 B2
(45) Date of Patent: Jun. 10, 2008

(54) SUBSTRATES FOR ISOLATING REACTING AND MICROSCOPICALLY ANALYZING MATERIALS

(75) Inventors: Jean I. Montagu, Brookline, MA (US); Roger Dowd, Natick, MA (US); David Root, N. Chelmsford, MA (US)

(73) Assignee: Decision Biomarkers, Inc., Waltham, MA (US)

( * ) Notice: Subject to any disclaimer, the term of this patent is extended or adjusted under 35 U.S.C. 154(b) by 0 days.

(21) Appl. No.: 10/524,614

(22) PCT Filed: Aug. 18, 2003

(86) PCT No.: PCT/US03/25685

§ 371 (c)(1),
(2), (4) Date: Nov. 2, 2005

(87) PCT Pub. No.: WO2004/018623

PCT Pub. Date: Mar. 4, 2004

(65) Prior Publication Data

US 2006/0134606 A1      Jun. 22, 2006

(51) Int. Cl.
*C12Q 1/68*      (2006.01)
(52) U.S. Cl. .......................................................... 435/6
(58) Field of Classification Search ................... 435/6, 435/4, 7.1, 7.92, 287.1, 287.3, 287.7; 436/518; 356/244, 246; 422/50, 55
See application file for complete search history.

(56) References Cited

U.S. PATENT DOCUMENTS

| | | | |
|---|---|---|---|
| 5,112,736 A | | 5/1992 | Caldwell et al. |
| 5,310,650 A | * | 5/1994 | McMahon et al. ............. 435/6 |
| 5,486,452 A | | 1/1996 | Gordon et al. |
| 5,491,097 A | | 2/1996 | Ribi et al. |
| 5,552,272 A | | 9/1996 | Bogart |
| 5,807,522 A | | 9/1998 | Brown et al. |
| 5,837,196 A | | 11/1998 | Pinkel et al. |
| 6,017,496 A | | 1/2000 | Nova et al. |
| 6,051,388 A | | 4/2000 | Bodenhamer |
| 6,197,599 B1 | | 3/2001 | Chin et al. |
| 6,207,369 B1 | | 3/2001 | Wohlstadter et al. |
| 6,210,878 B1 | | 4/2001 | Pinkel et al. |
| 6,329,209 B1 | | 12/2001 | Wagner et al. |
| 6,365,418 B1 | | 4/2002 | Wagner et al. |
| 6,381,013 B1 | * | 4/2002 | Richardson .................. 356/305 |
| 6,406,921 B1 | | 6/2002 | Wagner et al. |
| 6,472,224 B1 | | 10/2002 | Wischerhoff et al. |
| 6,475,808 B1 | | 11/2002 | Wagner et al. |
| 6,630,358 B1 | | 10/2003 | Wagner et al. |
| 6,861,251 B2 | | 3/2005 | Green |
| 6,921,637 B2 | | 7/2005 | Audeh et al. |
| 7,047,610 B2 | | 7/2006 | Cozzette et al. |
| 2002/0068157 A1 | | 6/2002 | Wischerhoff |
| 2002/0095073 A1 | | 7/2002 | Jacobs et al. |
| 2003/0228637 A1 | | 12/2003 | Wang |

FOREIGN PATENT DOCUMENTS

| | | | |
|---|---|---|---|
| EP | 0366241 | * | 2/1990 |
| EP | 0366241 A | | 5/1990 |
| WO | WO 98/20353 | | 5/1998 |
| WO | WO 99/07892 | | 2/1999 |
| WO | WO 00/33078 A | | 6/2000 |
| WO | WO 2004/063719 | | 7/2004 |

OTHER PUBLICATIONS

"FAST Slides Protocol", pp. 104-106, www.schleicher-schuell.com/bioscience.

(Continued)

*Primary Examiner*—Ann Y. Lam
(74) *Attorney, Agent, or Firm*—Fish & Richardson P.C.

(57) ABSTRACT

An immobilizing device for biological material comprises a rigid support (12) carrying a substrate layer (20, 20') of polymer having biological immobilizing properties, e.g. for amino and nucleic acids. Substantially solid ultra-thin substrate layers (20') having a thickness less than about 5 micron, preferably between about 0.1 and 0.5 micron, and micro-porous, ultra-thin substrate layers (20') having a thickness less than about 5 micron, preferably less than 3 micron, 2 or 1 micron are shown, which may be segmented by isolating moats M. The substrate layer is on a microscope slide (302), round disc (122), bio-cassette, at the bottom of a well of a multiwell plate, and as a coating inside a tube. Fluorescence or luminescence intensity and geometric calibration spots (420) are shown. Reading is enhanced by the intensity calibration spots (420) to enable normalization of readings under uneven illumination conditions, as when reading by dark field, side illumination mode. The reference spots are shown being printed simultaneously with printing an array of biological spots or with the same equipment Methods of forming layers of the device include controlled drawing from a bath of coating composition and drying, and spinning of C-D shaped substrates. Post-forming treatment is shown by corona treatment and radiation. Adherent metal oxides (14), silica-based materials and other materials are used to unite layers of the composite. In multi-well plates the oxide promotes joining of a bottom plate (95, 95') and upper, well-defining structure (94) of dissimilar material. The oxides (14) also provide beneficial opacity to prevent light entering the glass support, for applying potential to the substrate, etc.

70 Claims, 17 Drawing Sheets

OTHER PUBLICATIONS

FAST Slides S&S nitrocellulose slides, p. 1, Product Specifications, http://www.arraying.com (2005).

Ge, S. et al. "Monitoring of Bacterial Gene Expression Using Ollgonucleotide Microarray Analysis" Abstracts, 42nd Interscience Conference on Antimicrobial Agents and Chomotherapy. American Society for Microbiology, 2002.

Grace Bio-labs Oncyte Film Slides, Nov. 12, 1998.

Kukar et al., "Protein Microarrays to Detect Protein-Protein Interactions Using Red and Green Flourescent Proteins", Analytical Biochemistry 306, 50-54 (2002).

"New Chip on the Block", Laboratory Medicine, 30(3):180.

Onyiriuka et al., "Surface Modification of Polystyrene by Gamma-Radiation", Applied Spectroscopy, vol. 44, No. 5 (1990).

Pinkel et al., "High resolution analysis of DNA copy number variation using comparative genomic hybridization to microrays", Nature Genetics, 20:207.

Schleicher & Schuell, "Fast™ Slides" Oct. 2001.

Steinitz et al., "An improved method to create nitrocellulose particles suitable for the immobilization of antigen and antibody", Journal of Immunological Methods, 187:171.

Grace Bio-labs, "HybriWell™ Seal System", Nov. 12, 1998, http://www.gracebio.com/prodhybriseal.htm.

Grace Bio-labs, "MultiWell™ Press-to-Seal Arrays", Nov. 12, 1998, http://www.gracebio.com/prodpress.htm.

* cited by examiner

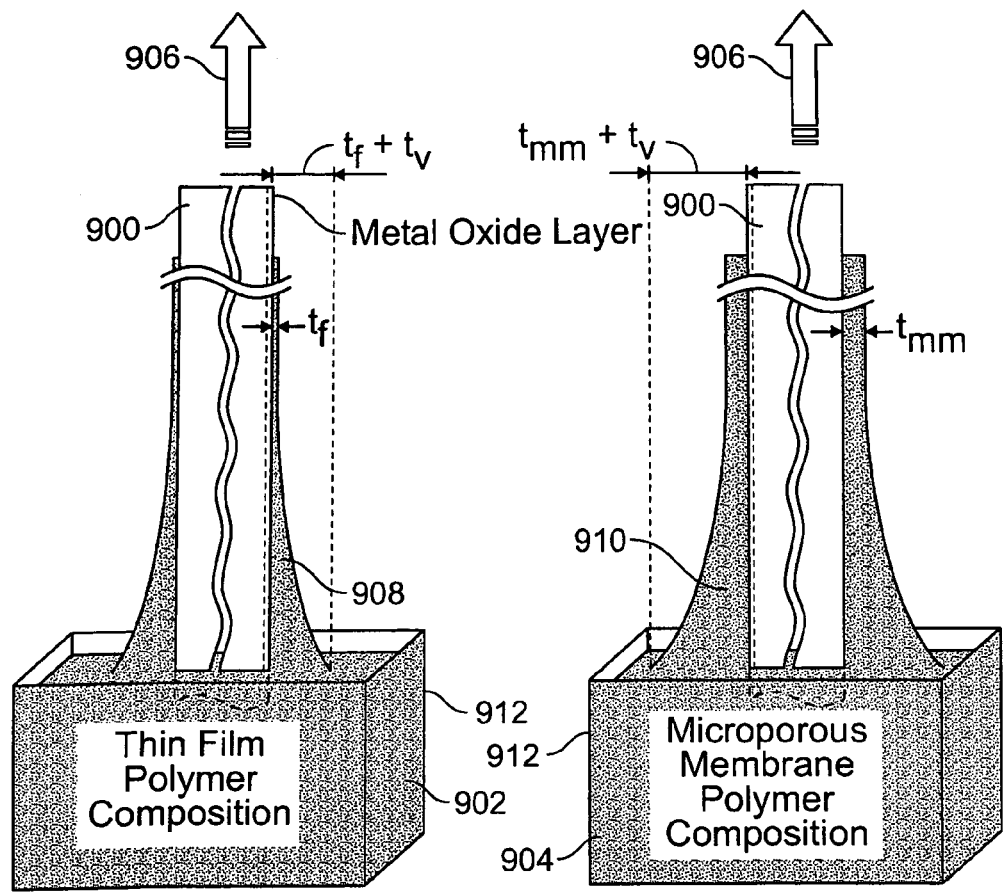
FIG. 15
FIG. 17
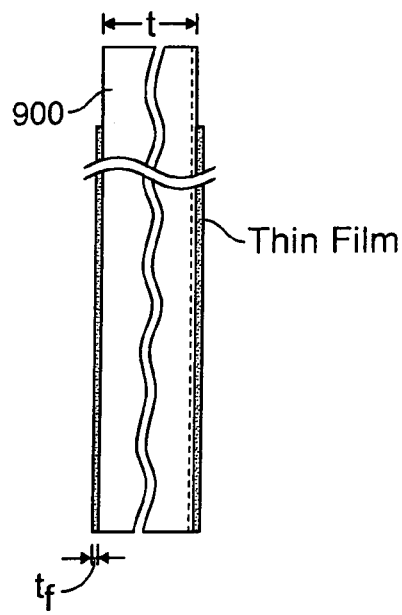
FIG. 16
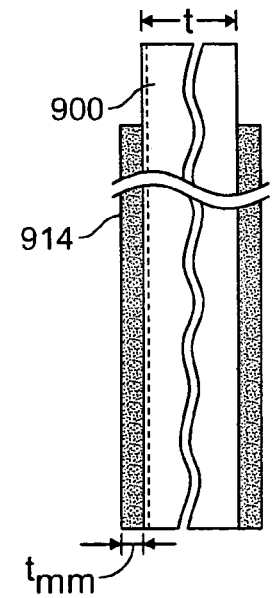
FIG. 18

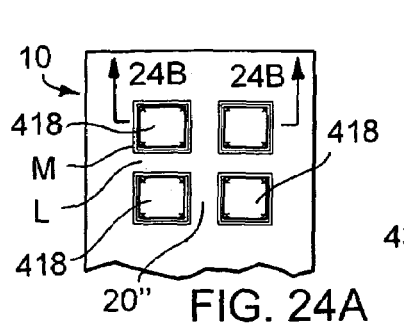
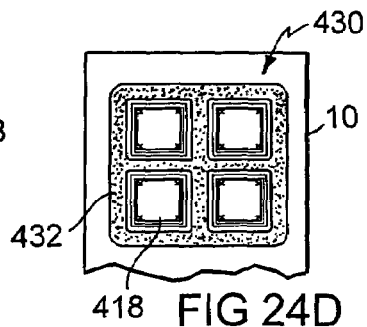
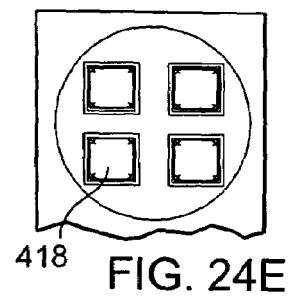
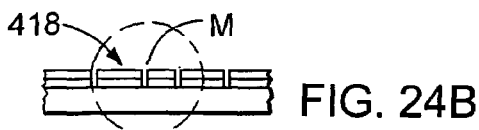
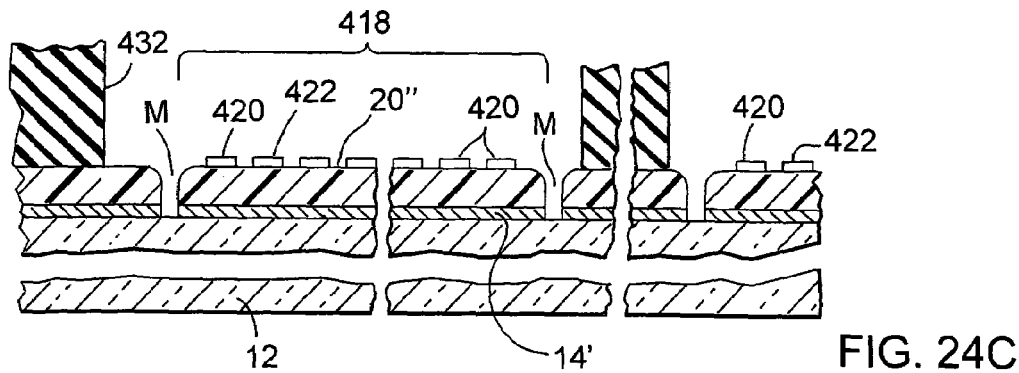
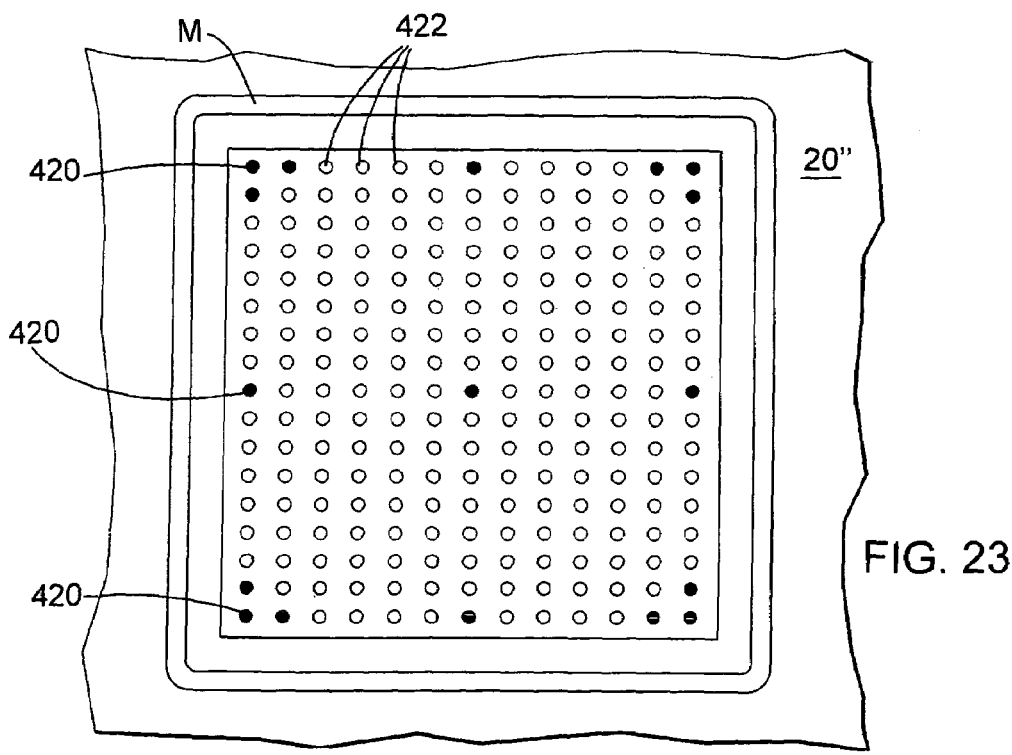

SUBSTRATES FOR ISOLATING REACTING AND MICROSCOPICALLY ANALYZING MATERIALS

TECHNICAL FIELD

This invention pertains to substrates for isolating, reacting and microscopically analyzing bio-materials, especially proteins, and genetic materials. The invention also pertains to methods for making and testing the substrates, to bio-array products employing the substrates, and to methods of binding, reacting, assaying and imaging materials on the substrates.

Embodiments of the invention in particular pertain to coated glass slides, multi-well plates and similar rigid supports that receive the protein or genetic material and retain the material in precise position while an assay is performed, the array is washed, and the altered array is analyzed for fluorescent emission. The invention also pertains to multi-well plate constructions as well as to tubes, bio-cassettes, disk-form substrates and other configurations.

Embodiments of the invention pertain to techniques for isolating, binding and discriminating between different bio-molecules and for establishing conditions for reaction.

Embodiments of the invention pertain to examination of tissue, for instance biopsies of potentially malignant tissue or of contaminated materials such as potable water, e.g. to enable detection of rare events.

BACKGROUND

The search for improving and extending the capabilities of optical analysis have long involved considerations of the substrate on which the specimen is supported during the analysis.

In the case of biological material, use has been made of polymeric substrates, in particular, porous substrates also referred to as "membranes" and "matrices," to immobilize the material while the material undergoes genetic analysis or is used for cell or protein research. Historically, porous matrices were first created as filters, to separate particulates contained within a liquid. In the process, a number of porous polymeric matrices were identified to have strong binding affinity for a number of bio-polymers. These matrices became the substrates of choice for cytochemistry and bio-polymer studies, especially where radioactive labels were employed.

The ability of nitrocellulose membranes (also referred to as "cellulose nitrate") to serve as substrates to bind single stranded DNA, i.e., to immobilize DNA, was demonstrated by Nirenberg in 1965 in flow-through assays. Such membranes were commonly formed using fibrous cellulose as a starting material.

Cellulose, to which nitrocellulose is related, is formed as a chain of glucose units, which is the universal building material for living cells. Nitrocellulose membranes benefit in this regard by relationship to cellulose, and have been commonly used substrates because of their molecular binding properties. The membranes have been used to bind cells, bio-polymers, proteins, genetic material and nucleic acids, as well as serving as substrates for non-biological chemicals.

The use of micro-porous polymeric membranes, in particular, nitrocellulose, for blotting bio-molecules from electrophoretically separated molecules was developed by Southern for DNA-DNA interactions. The technique is commonly called "Southern" blotting in honor of the developer. The other compass directions have been developed. "Western" blotting is a technique that has been employed to immobilize protein on an immobilizing substrate for protein-protein interactions.

Southern's need was for a method to identify the separated zones in electrophoretic separation. The blotting method employed micro-porous nitrocellulose to specifically identify the electrophoretically separated zones.

A brief outline of the original Southern blotting technique may help understand the general function of the nitrocellulose substrate:

A sample, in this case containing DNA, is separated on a gel media by electrophoresis and is denatured by treatment with sodium hydroxide.

A micro-porous nitrocellulose membrane is placed over the gel.

Blotter paper is placed over the membrane to absorb the water from the gel and a weight is added on top. The weight forces the water and separated molecules into the micro-porous membrane as the gel collapses beneath the membrane. This leaves an image on the membrane comprised of the separated bio-molecules.

DNA from the zones is bound non-specifically to the micro-porous nitrocellulose membrane.

The nitrocellulose membrane is washed and blocked by diffusional methods.

For performing an assay, the nitrocellulose membrane is then incubated with a solution of a known labeled DNA.

If the DNA added is an exact match to a zone of the DNA immobilized from the electrophoretic separation, the labeled DNA will bind and the zone will be labeled.

After successive washings, a visual image of the labeled zones then is prepared using X ray film if a radioactive label were used, thus identifying the zones.

Following the original development of Southern's techniques, in an effort to increase throughput, a trend developed to replace radioactive tracers with fluorescent tags, with the stimulated fluorescent emissions being imaged by optics. It was noticed, however, that available porous polymeric membranes, themselves, exhibited fluorescent emission over a wide spectral range. This fluorescent emission, as background noise, limited the use of polymeric membranes in fluorescent studies of proteins. While nitrocellulose membranes have been identified as one of the least offenders, still, when used as a substrate material, nitrocellulose has been found to have objectionable fluorescence that has limited both the accuracy of detection and the throughput of assays.

In the case of DNA, despite a continuing desire to employ polymeric membranes such as nitrocellulose, a way around the fluorescence problem was found, by spotting arrays on glass or quartz slides, that have relatively little background emission, using a layer of non-polymeric silane or GAP, and other such materials as adhesion promoters to which the biopolymer is directly bound. These adhesion promoter materials, despite their own significant problems, such as difficultly in obtaining a uniform thickness, noise contribution, and reactivity, have permitted significant success with small molecules. No similar technique has existed that is as effective for protein molecules, which are approximately 1000 times larger than DNA. Resort, still, has often been made to membranes of considerable thickness of porous nitrocellulose or other self-fluorescing polymeric immobilizing material, the material either being self-supporting or backed by a support. In the case of micro-porous nitrocellulose on a backing such as a microscope slide, typically the nitrocellulose has been at least 10 micron in thickness, and its self-fluorescence has remained a limiting factor for assay throughput. The significance to biology and to the clinician of the need to conduct higher throughput, large scale assays of protein arrays is discussed for instance in Chin et al., U.S. Pat. No. 6,197,599.

New insights are presented here about the substrates on which many of the known protein assays can be conducted. These insights lead broadly to techniques that increase throughput and achieve higher accuracy imaging of fluorescently- or luminenscently-labeled proteins and other bio-materials for large scale assays for research and for clinical diagnosis.

Some Prior Techniques with Nitrocellulose

Referring specifically to the practice of depositing spots of biological fluid on a solid or micro-porous surface to create a microarray, this has been widely described. In the case for instance of using glass slides bearing porous membranes of nitrocellulose, e.g. of 12 to 15 micron thickness, the supplier, Schleicher & Schuell, has recommended creation of each spot of the biological fluid with as much as 50 nl of fluid suspension, or more.

As a different nitrocellulose approach, using less suspension, spots composed of smaller amounts of liquid mixture of bio-molecules with nitrocellulose in a colloidal form or otherwise, have been formed on a glass or other support, where the nitrocellulose is either dissolved or in suspension in a common solvent. Additional solvents are introduced to cause desiccation of the deposit, resulting in a porous matrix that serves as an immobilizing structure for the intermixed biological material. This technique has been described by Pinkel in Nature Genetics, Volume 20, October, 1998, and by Audeh et al., U.S. Patent Application Publication 2002/0015958. These publications, involving very thin deposits or spots of the mixture of the bio-material with nitrocellulose on a support, have so far failed to advance the state of the practical art. These processes appear to have an inherent source of uncertainty or error, as they do not permit spot-to-spot evaluation of the contribution of the nitrocellulose or other immobilizing substrate material to the signal detected from the spots of fluorescently labeled proteins. In the technique, the fluorescent signal from a spot itself is necessarily the sum of the emission of the glass or other support, the porous nitrocellulose or other immobilizing material and the biological material itself. As these emissions are all combined, no simple method of separation exists for the signal from the biological material from such spots of biological/nitrocellulose material.

In more common assays with the available much thicker but continuous membranes of nitrocellulose mentioned, and with other immobilizing polymers, subtraction of perturbation noise is commonly used. Owing to the general uniformity of the thickness of such substrates across the supports, standardized software can measure the emitted noise signal from the unspotted membrane and automatically subtract a value approximately representing its noise signal from the total signal derived from the spot. In the case of the spotted Pinkel or Audeh et al. mixtures, the local vicinity beyond the spot does not contain a continuation of the substrate material that contributed to the fluorescent background at the spot, so the subtraction technique cannot be used to remove the effect of the substrate material. The magnitude of fluorescent energy as measured by the level of signal detected by a confocal scanning microscope such as the Affymetrix 428 Scanner has shown that a substantial error in the measurement of sample fluorescence can be introduced by the Pinkel or Audeh et al. process, and no successful variation of the technique that allows some form of subtraction has yet been found.

Ultra-Thin, Low-Noise Immobilizing Substrates

A new and different approach is presented to immobilizing and imaging fluorescently labeled biological materials. It employs a continuous, ultra-thin layer of a substrate of polymer that has biological binding properties, for instance, nitrocellulose. The technique is effective, using protein-immobilizing polymeric substrates, to enable imaging of fluorescently labeled proteins. The technique has other potential widespread uses, such as with proteins labeled with luminescent tags, and with other bio-materials labeled with fluorescent or luminescent tags. The technique may be used to advantage with viruses, peptides, antibodies, receptors, and other proteins; with a wide range of other labeled biological materials including plant, animal, human, fungal and bacteria cells; with nucleic acids, as a very practical substrate, with fewer problems than other materials, e.g. for cDNA clones, DNA probes, oligonucleotides including synthetic oligonucleotides and polymerase chain reaction (PCR) products; and with labeled chemicals as well. It has the attractive potential of being a low-cost, practical substrate of choice over the prior materials, such as GAP for instance, (GAP, because of high reactivity, requires costly and time-consuming precautions to avoid contamination.)

It has been found that a superior immobilizing substrate, suitable for receiving deposit of an array of spots of bio-polymers, is provided by a continuous ultra-thin layer of polymeric substrate material having biological binding properties, i.e., (a) in a 3-dimensional micro-porous form, an ultra-thin layer of thickness of less than 5 micron, down to less than a micron in thickness or approximately equal to the size of the pores, with pore size respectively from about 3 micron to ½ micron, or (b) as a solid surface coating, of a thickness less than 5 micron, less than 3 micron or thinner, down desirably to submicron thicknesses, e.g. 0.1 to 0.5 micron, or even as a molecular layer.

Polymer substrates of these dimensions are found useful to immobilize proteins and the broader categories of materials mentioned. Further, it is found that such continuous, ultra-thin polymer layers can readily be formed.

The uniform ultra-thin layer of biological-material-immobilizing polymer on a rigid substrate has been found to be capable of enduring the conditions of printing of spots of bio-polymers in precisely known positions, of conducting the assay, of application of successive washes, and, following handling, of being microscopically analyzed by stimulated emission. The ultra-thin layer is found to significantly reduce background noise attributable to parasitic fluorescence of the immobilizing material and to otherwise offer advantages due to considerations that will be described.

It is found also that a continuous ultra-thin layer can have such uniformity that it enables its signal contribution from its area lying beyond the spotted material to be subtracted from the measurement of the spots in a reliable manner, further increasing the quality of signals from that obtainable by prior techniques.

Those skilled with respect to protein-immobilizing membranes may have supposed that a significant depth of porous nitrocellulose or other protein-immobilizing substrate, i.e., 10 micron or more in available commercial products, would be important. Those skilled may have supposed that the significant depth of present commercial membranes was required to enable forming a uniform and durable membrane that could survive printing of spots, conducting the assay, applying successive washes and handling the unit through analysis, while still holding the deposited spots reliably in their precisely known places. Or, those skilled may have believed that current commercial thicknesses of the substrate were required to enable reliable manufacture, or to provide a liquid-receiving volume below the deposit sites to enable the carrier liquid to drain downwardly. Or, those skilled in the art may have believed a significant thickness of the immobilizing substrate was required, to provide a thickness-to-variance-in-thickness ratio sufficient to enable a reliable subtraction technique for correcting for auto-fluorescence, etc.

It has been found that no such requirements are in fact necessary. It has been found that durable, ultra-thin continuous substrates of polymer having biological binding properties can be readily fabricated of less than about 5 micron thickness, and that spot formation and precision of location is not adversely affected by the steps of spotting, assaying, washing, handling and analysis.

It has been found that, using coating techniques that are conventional for thin coatings in other contexts, the inherent variation in thickness of the polymer coating is sufficiently small, relative even to the small overall thickness of the ultra-thin substrate, that a signal from the adjoining unspotted area of the continuous coating may be used in the described subtractive techniques to enable acquisition of superior microscopy results.

It has been found that a solid (non-porous) film of 3 micron, down to thickness under 75 nm, even down to molecular thicknesses, of immobilizing polymer substrates, and in particular, of nitrocellulose, can be formed and successfully employed in high throughput protein and other bio-material assays.

It has also been realized that such ultra-thin substrates may be altered after forming as a coating or substrate, as by corona discharge, atomic particle or radiation bombardment or by controlled energy excimer laser beam treatment, to improve binding and immobilization topology or conditions.

In making such developments, the importance has been recognized of the fact that bio-molecules bind to the surface of the nitrocellulose or other immobilizing polymeric material, while parasitic fluorescence is emitted from the entire volume or bulk of the material illuminated by the inspection technique. When microarrays have been spotted on commercial membranes (10 micrometer or thicker membranes), the biological material normally accumulates at the outer portion of the thickness of a membrane supported on rigid non-porous support, e.g., on only 30% or 40% of the total thickness of the membrane. This is due to the fact that flow-through conditions for the bio-molecules are obstructed when a very small volume of volatile fluid supporting the biological matter is deposited. Bio-polymers and the carrying fluids wet the surface, the necessary phenomenon, and saturate the pores to a shallow depth and block further penetration as the liquid carrier separates, migrates beyond or evaporates.

The importance has been realized of the fact that polymeric bio-immobilizing materials such as nitrocellulose behave in an approximately linear manner and emit fluorescent radiation in relationship to the volume of material exposed to the excitation beam and the level of excitation and that a layer of the material of thickness limited to less than 5 micron and preferably less than 3 micron thick and in important cases even less than 1 micron thick can provide significant advantage.

In the case of ultra-thin micro-porous substrates provided here, the percentage of the volume of porous material that actually bears the biological material, relative to the total volume of the substrate material presented to the collecting optics, may be greater than 50% and advantageously in many case, greater than 75%, unnecessary volume of the material and its deleterious fluorescence being avoided.

Experimentally it has been determined that the parasitic emission of fluorescent light increases with the thickness of a micro-porous membrane with thickness of 1, 2, 3, 4, 7 and 14 micron.

It has further been realized that the parasitic fluorescence emission of a porous membrane of a given amount of nitrocellulose or other biology-binding polymeric material per unit area of the support structure can be many times greater (measured in one case to be approximately 6.4 times greater) than that of the same material presented as a transparent solid film. The nitrocellulose in its translucent/semi-opaque 3-dimensional porous membrane form is observed to absorb excitation radiation to a much greater degree than the same material in transparent semi-crystalline form. In addition, a relatively thicker porous membrane also reflects or scatters some of the excitation energy to a much greater degree than a thinner and especially, transparent, membrane.

Furthermore, it has been observed that an ultra-thin transparent solid membrane of polymer having biology binding properties, in reflecting a minimum amount of excitation energy, minimizes the exclusion requirement of the filter that is required in a collecting system to separate the fluorescent emission energy to be detected from the excitation energy.

It has also been recognized that the strength of the fluorescent radiation signal emitted toward the collecting optics by the fluorophore-tagged bio-polymers bound to the immobilizing polymeric material is not only a function of the quantity of the bio-polymer present and of the energy of the excitation source. It is also a function of the location of the emitting bio-molecules with respect to the top surface of the immobilizing medium. Bio-molecules may be located on the outer surface or buried to varying depths of a 3-dimensional membrane structure. Fluorophores attached to the molecules located within a 3-dimensional matrix below the outer surface are twice handicapped when compared to similar molecules on the outer surface. The energy intensity penetrating a semi-opaque, diffusive material, such as a highly porous polymeric material, decreases in function with the distance traveled and the absorption characteristics of the medium. In a similar manner, the stimulated fluorescent light from excited molecules buried within the matrix is absorbed to some degree or scattered before exiting to be collected by the optical system. The deeper a particular fluorophore is in a 3-dimensional porous polymeric structure, to some degree, the less intense will be its fluorescent emission at the collecting optics.

Accordingly, the novel, solid ultra-thin polymer film of immobilizing nitrocellulose or other bio-material-immobilizing polymer material is seen to be of considerable importance. It is recognized that a surface of solid nitrocellulose or other solid immobilizing polymer may usefully provide sufficient binding sites (for bio-polymers, cells or small fragments of tissue or other material to attach to), on a single plane, in a deposited spot of useful size for an array to be assayed. A number of binding sites equal to that of a surface folded in a small pore, 3 dimensional structure (such as that of a micro-porous polymer membrane) is obtainable with a solid coating by increased spot size. It is recognized that binding sites on a general plane in some ways offers better binding opportunity, e.g. equal opportunity for attachment of bio-polymer molecules to all sites, than is possible within an equivalent surface tightly folded in a 3-dimensional form. This is especially true in comparison to micro-porous polymer structures in the case where pore size may vary, and in cases where bio-deposits are dependent upon concentration, drying conditions, etc. of the spotted fluid. Especially for large protein molecules, this consideration is believed to be obtainable from assay to assay by performing assays of the proteins or other bio-polymers on solid, or modified solid ultra-thin coatings of immobilizing polymer material.

Continuous ultra-thin micro-porous polymer substrates, and solid substrates of bio-material-immobilizing polymer material, supported on glass, metal or plastic, used to immobilize fluorescently-tagged or luminenscently tagged bio-polymers, can achieve superior signal-to-noise ratio and other advantages that provide superior information or diagnostic efficacy.

Excellent analysis results have been obtained employing nitrocellulose as the ultra-thin micro-porous polymer material or as an ultra-thin solid polymer coating, while very desirable results are also realized to be obtainable with polystyrene. Other ultra-thin polymers that have biological binding properties may also be used e.g., cellulose acetate, cellulose triacetate, ethyl cellulose, activated nylon, polytetrafluoroethylene (PTFE), polyvinyl difluoride (PVDF), polyamides, polyvinylchloride, di-vinyl benzene and agarose, including copolymers and blends.

In one specific embodiment, a continuous micro-porous polymer matrix thinner than about 5 micron, and preferably as thin as 3, 2 or 1 micron or less, is provided to support bio-polymers under study. With the use of this structure, while the parasitic noise is reduced according to the thickness of the ultra-thin, polymeric substrate, it is found that the fluorescing signal is minimally reduced in comparison to use of the presently available commercial materials, the transferred volume of fluid not being appreciably altered in its course into the thickness of the ultra-thin material. Ordinarily the 3-dimensional matrix offers a larger binding surface (more bio-material binding sites) than the footprint of the same support.

Another important embodiment, however, is the ultra-thin, solid, i.e. non-porous, coating of polymer with biological binding properties, thinner than 5 micron, preferably less than 3 micron and preferably as thin as 2, 1, 0.5 or 0.1 micron, or even at molecular thicknesses, deposited on a rigid supporting medium of extremely low fluorescent properties, such as low fluorescence glass, fused quartz, ceramic, PMMA, polystyrene, other plastic or metal. The overall background-perturbing effect of such a bio-compatible substrate is preferably of the order of or even less than that of its supporting rigid structure.

In these embodiments, the number of photons necessary to obtain a statistically reliable signals dictates the spot area dedicated for attachment of the bio-polymers. Preferably, this area is approximately a spot with diameter greater than 100 micron in diameter and less than 1,000 micron, preferably less than 500 micron. In many cases, the preferred spot sizes of the bio-polymers are below about 500 micron, for instance 100 to 400 micron, 150 micron and 300 micron being common dot sizes. This enables the formation of suitable microarrays with provision for the needed sequence of dilutions and provision of process reference spots to enable large scale, high speed throughput of the assay and analysis. The system is more economical, with respect to amount of biological material required per spot, e.g. less than one nl per spot required, in comparison to prior art schemes of spotting on 10 or 12 micron or greater thickness micro-porous nitrocellulose on glass, for which a recommended amount by one supplier for an individual spot has been as high as 50 nl or higher.

Methods of manufacturing such ultra-thin, immobilizing polymer layers are provided that are found to produce particularly good substrates.

Novel methods are provided of depositing ultra-thin coatings of nitrocellulose or other immobilizing polymer, i.e. material having biological binding properties, on a suitable solid support, in many cases, a microscope glass slide having approximate dimensions of 25×75 mm, by about 1 mm thick, as will now be described.

Blank glass microscope slides are obtained, such as part No. 2951 from Erie Scientific Co. in Portland, N.H., with a short frosted section at one end. These are pretreated by applying a surface adhesion promoter and/or a layer permitting the application of indicia to the slide for important purposes such as identification and serialization, registration for microscopic analysis or other processes, provisional classification markings, or simply for presentation or branding. A number of choices can be made. Two preferred embodiments are:

(a) A painted/covered region is applied over the frosted area with or without the addition of a 1 to 3 mm (and preferably 2 mm) wide frame tracking the outer periphery of the slide. The painted region over the frosted area may later be laser-marked with identification and serialization or other marking as desired. The process used may impart non-serialized markings.

(b) A coating is applied over the entire slide on the frosted surface side by vapor deposition or sputter coating e.g. tantalum followed by air oxidation to form a thin layer of tantalum oxide in order to provide opacity ranging between 10% and 90% with respect to a nominal laser wavelength of 635 nm. The coated region over the frosted area is suitable later to be laser marked with identification and serialization or other marking including non-serialized markings. Also the region to be spotted may be divided into sub regions (or islands), e.g. by removing a circular or square moat of tantalum oxide surrounding each individual array. Such isolated region may serve to protect the spotted array portion from delaminating when an adhesive gasket is applied outside of the moat during experiments.

In an alternative manner laser marking and segmentation may be performed following coating.

Preferably a laser will be used with wavelength absorbed by the coating to be removed and not absorbed by the material of the support, glass or other.

Laser ablation of the coating over the frosted region may serialize the slides or add identification or registration markings for automatic optical unit or information retrieval. Ablation enhances data acquisition reliability in processes using a variety of equipment including commercial bar code readers.

Advantageously, after application of an adhesion promoting layer, at least one durable sensitivity calibration spot may be applied. The sensitivity calibration marking is provided to act as a fiduciary marking for geometrical reference, and by suitable choice of its material, serves as a standard fluorescence reference in order to determine and accommodate long-term variations in optical instrumentation.

Similar fluorescing calibration spots are applied on the outer surface of the completed substrate. In advantageous cases they are applied in a low-density pattern interspersed with high density biological spots, and used for calibration, or for normalization in instances where uneven excitation illumination may occur, e.g. when employing illumination at an angle to the normal to the plane of an array, as in imaging via dark-field reflectance mode.)

Preferably, the calibration compound is selected to have a broad fluorescence spectrum. A temporally stable material, such as polyimide polymers (Kapton), exhibiting broad band, standard fluorescence, i.e., yielding fluorescence at a wavelength in reliable manner, is selected as the reference fluorophore and deposited on a slide surface with solvent followed by solvent evaporation. Typical spot diameters may be 150 micron and 300 micron, and can be applied using commercially available biology printers (sometimes referred to as "spotters" or "microarraying instruments".) The precise amount of material deposited is unimportant since polymers such as Kapton are optically opaque, and detected fluorescent emission from the polymer occurs at or near the surface of the deposited material giving reproducible quantum yields.

The use of the calibration material applied to each slide allows for instrument self-calibration, i.e., auto calibration, per slide. A distribution of calibration spots, in number and spacing dependent on the non-uniformity of excitation illumination incident on a slide, may be employed. As few as six distributed in an array may suffice although larger numbers also are employed, depending upon the characteristics of the reader system.

A preferred process for preparing the glass microscope slides includes the removal of all particulates and most organic matter via mechanical means using solvents and detergents. The slides are subsequently left to dry in air. The active surface (as defined as the surface with frosted area) is then subjected to ozone treatment, e.g. to remove residual organic matter and enhance the adhesive properties of the surface. The ozone reactions may be activated using corona exposure or UV illumination. In a preferred embodiment, the ozone/corona treatment is induced by translating the slide at a speed between 2 and 8 cm/min (preferably 4.4 cm/min) past a corona discharge while exposing surface to be treated normal and approximately between 1 and 4 cm (preferably 2 cm) to the jet of a standard 2.5 cm. round head of a laboratory corona treater (model BD-20AC from Electro-Technic Products Inc., Chicago, Ill.) operating near its optimal level. Preferably the pressure, temperature, and humidity are held within the human comfort zone of 65°-72° F., one atmosphere, and humidity between 30 and 70%.

Alternately, such slides are cleaned of debris as well as of any biological products such as by washing them for approximately 30 minutes in an ultrasonic bath with a detergent and subsequently holding them in an oven at about 450° C. for approximately 8 hours.

If the preferred embodiment of pretreatment (a) above is used, the slides are then coated with a less than 1 μ thick layer with colloidal silica or soluble silicate. For this purpose, LUDOX CL, LUDOX CL-X, or LUDOX TMA suspended in water is employed, available from Sigma-Aldrich Co. An equivalent product may be obtained from other sources. For this purpose, slides are held for 1 second to 1 hour in a bath of 1% to 10% (preferably 3.3%) colloidal silica and exhumed (drawn from the bath) preferably at a constant rate between 0.1 and 10 in/min (preferably 0.5 in/min), along a path parallel to the plane of the microscope slide to form a coating (referred to as a "drawn coating"). This is followed by drying in air. Preferably, the environmental pressure, temperature, and humidity are held within the human comfort zone as previously described. In producing a final substrate layer upon which the biological material is to be immobilized, the slides are preferably submerged in a solution of desired substrate material and withdrawn from the solution at an appropriate uniform rate, to form a drawn substrate layer. This coating procedure is performed under defined environmental conditions and using a solution adapted to such standardized conditions.

The final coating fluid may be selected from a number of possibilities. Three preferred embodiments employ compositions that form polystyrene films, nitrocellulose films, and nitrocellulose microporous membranes. The coating solutions can be employed over a wide range of concentrations. Advantageously the solutions can be normalized to a given set of operating conditions for production advantages. In the examples to be given, the three compositions of nitrocellulose and polystyrene are normalized to a set temperature of the still environment and a set draw rate, specifically 26° C. and 1 in/min, respectively, for producing films of 0.1 μ thickness of polystyrene and nitrocellulose and an adherent porous membrane of less than 5 μ of nitrocellulose.

In a specific example, polystyrene film is produced by dissolving 5 gm of polystyrene pellets from Dow (pre-dried between 90° and 100° C. for 24 hours) in 100 mL of amyl acetate with low shear mixing. Low shear mixing is obtained by rolling the ingredients in a glass vessel at 4 rpm. Slides are submerged in a vat held at 26.0°±0.5° C. containing the composition and subsequently withdrawn at a uniform rate between 0.1 and 10 in/min, preferably 1 in/min. Optimally, the process is performed in a 5 cubic feet hood with a controlled atmosphere of 33% humidity and 26° C. with draw rate matched to the composition and the controlled process conditions. Following slide withdrawal, the processed slides are kept in the hood for 1 to 5 minutes. To reach a desired thickness of the coated slide, more than one dip may be employed.

In an embodiment for producing nitrocellulose films, 1.33 gm of nitrocellulose and 0.1 gm of dehydrated tin (II) chloride ($SnCl_2$) are dissolved in 100 mL of amyl acetate. Slides are dipped into (submerged in) a vat held at 26°±0.5° C. containing the composition and withdrawn at a uniform rate between 0.1 and 10 in/min, preferably 1 in/min. Optimally, the process is performed in a 5 cubic feet hood with a controlled atmosphere of 33% humidity and 26° C. Following slide withdrawal, the processed slides are kept in the hood for 1 to 5 minutes. To reach a desired thickness of the coated slide, more than one dip may be employed.

In an embodiment to produce nitrocellulose microporous membranes, 4.14 gm of nitrocellulose and 0.1 gm of dehydrated tin (II) chloride ($SnCl_2$) are dissolved in 55.6 mL of methyl acetate, 26.3 mL of ethyl alcohol, and 13.6 mL of butyl alcohol, 2.94 mL of water, and 1.11 ml of glycerol. Slides are dipped (submerged in) into a vat held 26.0°±0.5° C. containing the composition and subsequently are withdrawn at a uniform rate between 0.1 and 10 in/min, preferably 1 in/min. Optimally, the process is performed in a 5 cubic feet hood with a controlled atmosphere of 33% humidity and 26° C. Following slide withdrawal, the slides are kept in the hood for 2 to 5 minutes. To reach a desired thickness of the coated slide, more than one dip (i.e. immersion) may be employed.

In other embodiments for each type of coating, tin (II) chloride ($SnCl_2$) may be omitted, and other solvents may be substituted for the solvents listed above. Acetone, DMSO, or ethyl acetate are commonly used as alternate solvents for nitrocellulose and polystyrene.

In preferred embodiments, slides prepared as described above are surface treated to enhance the their binding capacity to biological material. In a preferred embodiment, corona treatment is induced by translating the slide at a speed between 2 and 8 cm/min (preferably 4.3 cm/min) while exposing the surface to be treated normal to the jet of a standard 2.5 cm. round head laboratory corona treater at a distance of approximately between 1 and 4 cm. The laboratory corona treater (model BD-20AC from Electro-Technic Products Inc., Chicago, Ill.) should be operated near its optimal level. Preferably the environmental pressure, temperature, and humidity are held within the comfort zone as described previously.

Possible contaminants (coatings or deposits) on the backside of the slide that may become loose in further processing must be removed. The backside of the slide may be cleaned during or after dipping and pulling from the vat or prior to packaging. Preferably, the finished slides are stored in dry nitrogen.

If a solid, ultra-thin, immobilizing polymeric film is desired, it is desirable to ensure that no liquid miscible with the solvent such as Amyl Acetate and having slower evaporation properties is present.

If a porous or 3-dimensional ultra-thin membrane is desired, water or another common porogen is added to the Amyl Acetate or other solvent to produce the pores. This is a technique known to those knowledgeable in the art.

Various solvent/nitrocellulose concentrations, etc. are listed in Chapter 5, pp. 116-157 of "Synthetic Polymeric Membranes" by Robert Kesting—McGraw-Hill, 1971, the book hereby incorporated by reference in its entirety. For polystyrene, preferred solvents are methylene chloride and acetone. For polystyrene, as well as PVDF and many of the other immobilizing polymer substrates, other suitable solvents are dimethylformamide (DMF) and dimethylsulfoxide (DMSO). Chloroform and other solvents recognized for the respective materials, as determined from readily available references, may be used.

In other embodiments, other techniques are employed to mass-produce the ultra-thin coatings of nitrocellulose or other bio-material-immobilizing polymer material, as by Chemical Vapor Deposition (CVD).

While it is presently believed that ultra-thin layers of nitrocellulose and polystyrene have particular benefit, and are per se novel as described, also, as has been noted, other bio-material-immobilizing polymers in molecular or colloidal form, can be formed in similar manner to make ultra-thin, immobilizing polymer coatings on bio-chips. Typical of such materials, as noted, are cellulose acetate, cellulose triacetate, ethyl cellulose, activated nylon, polytetrafluoroethylene, polyvinyl difluoride (PVDF), polyamides, polyvinylchloride, di-vinyl benzene and agarose, including copolymers and blends.

It is further recognized that techniques that have been developed in the optical industry, to produce elements having optical properties, may in novel manner be brought over to produce the ultra-thin polymeric, bio-material-immobilizing substrates themselves, such as by forming an ultra-thin layer of solid polystyrene upon a glass microscope or slide support, e.g. to form a surface waveguide for exciting radiation. Importantly, techniques from the optical industry are also used in novel manner to provide adhesive-promoting primer layers on a rigid support, such as metal or metal oxide coatings. Similarly such coatings have other novel functions such as blocking passage of unwanted radiation between the substrate layer and its rigid support and applying electrical potential. These are formed prior to applying the ultra-thin polymeric, bio-material-immobilizing layer, and as described below, are found useful for other purposes.

Improvements in Forming Ispecting and Using Substrates

Beyond the issues of low fluorescence noise from substrates to which biological material is bound, new concepts are also presented here about substrates and their supports for isolating, bonding and reacting bio-molecules, and more generally for high accuracy optical analysis of small samples and for detecting rare events in biological tissue and other materials.

It is realized that adhesion promoters, particularly, adherent metal oxides such as tantalum or aluminum oxide, soluble silicates such as sodium silicate, and colloidal silica, (which have optical transmissive, absorptive and electrical properties developed for use in other fields) are useful for new and important biology analysis functions, according to other aspects of the invention. The functions relate both to microscopy and to the manipulation and reaction of bio-molecular and other bio-materials. They serve the important function of being united to adjacent layers, while providing new functionality in support of bio-microscopy.

As previously indicated, according to an aspect of the invention, tantalum or aluminum oxide, a soluble silicate such as sodium silicate, or colloidal silica, as well as other similar adherent metal oxides, used as intermediate layers, enable union of inorganic support materials, such as glass, fused silica, ceramic, silicon and metals such as gold, aluminum, silver, on one hand, with, on the other hand, organic materials, including polymeric materials, capable of immobilizing or being otherwise compatible with bio-molecules, e.g. nitrocellulose, polystyrene, cellulose acetate, ethyl cellulose, activated nylon, polytetrafluoroethylene, polyvinyl difluoride (PVDF), polyamides, polyvinylchloride, di-vinyl benzene, agarose, and including copolymer and blends of such organic materials, as well as fluorescently stable reference polymers such as polyimides (Kapton). Likewise, an adherent layer, e.g. one of the metal oxides, can be a compatibilzing an adherent middle layer between one class of organic material and another class of organic material, each of which bonds better to the adherent layer than to the other. An example is a polymeric material suitable to provide a dimensionally stable structural support such as polycarbonate, and the listed organic materials suitable for providing a deposit-receiving or immobilizing surface for bio-molecules and other bio-materials, including cells and tissue fragments, etc. It is further found that adherent metal oxides such as tantalum oxide can be deposited in a wide range of controlled thickness without appreciably affecting their adhesion properties for such uses, and that important new functions can be achieved with the material. Deposited thickness causing almost complete absorption and almost 90% of normal incident light from a red laser at approximately 635 nm, have been found to exhibit reliable adhesion properties between glass and nitrocellulose film and other membranes such as polystyrene film. Thus the material is useful in both reflectance and transmission imaging modes With tantalum or aluminum oxide, sodium silicates, or colloidal silica or another adherence promoting layer that is appropriately transparent to the wavelength utilized, along with employing substrate and support materials that are likewise transmissive, supports for biological material are provided that enable excitation and inspection of biological or chemical reactions from different sides of the support, from opposite sides, i.e. in both reflectance and transmission modes, as well as from the edges.

With a deposit of functionally opaque thickness of tantalum oxide or other adherent, light-absorbing material, supports for biological material are constructed such that the inspection of biological or chemical reactions is observed from only one side, with the benefit of blocking optical perturbation or polluting effects which may originate in the supporting substrate, such as fluorescence or luminescence. By blocking most incident radiation from reaching the support, most of such effects are not stimulated in the support, and such effects, to the extent stimulated, are substantially blocked from being transmitted from the support to the associated vision instrumentation. Likewise stray light reaching the support or light intentionally applied is blocked from reaching the instrumentation.

This feature of the invention ties in with an additional aspect of the invention, the modification of the surface of polymer substrate films, such as nitrocellulose or polystyrene, to enhance affinity or binding properties for the biomaterial or molecules. The modification may be to change the topology, the chemical nature or the charge state of the surface. In advantageous cases, the substrate material is attached to the rigid substrate via an adherent conductive layer such as the tantalum oxide and/or sodium silicates or colloidal silica. Surface modification conditions to enhance the binding affinity of the surface to biological molecules such as protein or DNA or any molecule or natural or synthetic oligonucleotides can be corona treatment, flame treatment, or bombardment as with ions, electrons or atomic or sub-atomic particles, or radiation including gamma rays or X-rays.

Another aspect of the invention is the use of the conductive tantalum oxide layer or other adherent, conductive layer or coating to establish an electrically polarized outer surface on the substrate. A positive electrical charge potential established on the layer produces a similar potential on the nearby substrate surface. This can attract to the surface negatively charged particles or ions or molecules or polynucleotides or artificially charged viruses or bacteria and/or can repel positively charged, similar molecules or particles. This capability is employed to select from similar molecules or particles according to their electrical charge.

Also, since no electrostatic force acts upon molecules with neutral potential, these are not attracted to or repelled from the surface. Thus a powerful sorting mechanism is now provided to attract and/or separate molecules or particles according to their electrostatic charge.

Transparent, electrically conductive coatings (e.g. indium oxide) and semi-conductive layers may be applied in the support sandwich for desired effects, depending upon the application. Any of these features are advantageously incorporated in novel devices to support biological reactions, including:

Supports in the shape of microscope slides, typically planar of approximately 25×75 mm width and length, 1 mm thickness.
  Supports in the shape of bio-cassettes, e.g. those of various common configurations.
  Supports in the approximate form of CD disks.
  The wells of multi-well plates.
  Reaction tubes.

A further aspect of the invention relates to the bonding of a bottom member to the upper bottom-less structure of a micro-well plate. On a bottom plate of glass (or organic material) a surface pattern of tantalum oxide or other adherence-promoting layer is applied. It may be in a pattern which matches the pattern of the lower edges of the bottom-less upper structure of the micro-well plate being assembled. This facilitates the manufacture of the composite well-plate, enabling the upper structure to be of material (e.g. polystyrene) that is adhesively incompatible with the bottom plate (e.g. glass). The spaces between the pattern may be treated to carry ultra-thin immobilizing layers as described.

In a related aspect of the invention, an adhesively incompatible support plate, e.g. of glass, intended to form the bottom of a multi-well plate by bonding to the bottom-less upper structure, is coated with a film of an adhesion promoter, e.g. the tantalum oxide and/or colloidal silica or sodium silicates discussed, followed by application of an upper film of polystyrene or other substance that is adhesively compatible with the upper structure, as well as being capable of performing as an immobilizing substrate. The bottom-less upper elements of the micro-well plate may thus also be of polystyrene and joined to a uniformly coated glass. The union may be enhanced by heat or as well as by the temporary presence of a solvent such as Amyl Acetate or the temporary presence of a solution of polystyrene in such a solvent.

The glass surface, coated with a thin film of polystyrene, may have its surface adhesion enhanced as described above, e.g. by corona discharge, or rendered porous, to serve as a bio-material receiving substrate at the bottom of the well.

A uniform film of polystyrene coated over the adhesion promoter on the glass plate, may be an ultra-thin layer as previously described, and its areas within the grid of the multi-well plate may thus be suitable for receiving deposit of bio-molecules as previously discussed.

The desirable glass bottom micro-well plates can be reliably manufactured and provided with the layers for the various features described above in relation to glass support structures for immobilizing, reacting, assaying and analyzing bio-material. Similar processes are applicable to other choices of plastic material for the micro-well plates.

Important aspects of the invention are summarized as follows.

A device for immobilizing biological material is provided comprising a polymer substrate layer having biological immobilizing properties, preferably for protein or nucleic acid, the substrate layer deposited on a rigid support, and having an outer deposit-receiving region exposed to receive the biological material, wherein the substrate layer is ultra-thin, having a thickness less than about 5 micron.

Preferred embodiments of this aspect of the invention have one or more of the following features.

The substrate layer has binding properties for the biological material.

The rigid support defines a straight support surface e.g., a planar surface such as that of a microscope slide or a cylindrical surface, and the substrate layer is a drawn coating applied directly or indirectly to the rigid support in the direction of the straight surface, preferably drawn substantially according to FIG. 14, described below.

The deposit-receiving region of the substrate layer is in a surface-treated state for enhanced adhesion of deposits of biological material thereon, preferably the surface treatment being that provided by a corona treater.

At least one intervening layer lies between the rigid support and the ultra-thin polymer substrate layer, the intervening layer adherently joined on each of its oppositely directed faces to substance of the device, e.g. immediately adjacent materials on opposite sides of an intervening layer are not as adhesively compatible with each other as each is with the intervening layer.

The intervening layer is an adherent oxide of metal, preferably an oxide of tantalum or aluminum, or a silica based material, e.g. colloidal silica or a soluble silicate such as sodium silicate.

The intervening layer is of substance selected from the group consisting of silane, epoxy silane, polylisine, PEI, GAP, adherent metal oxides, colloidal silica and soluble silicates.

A straight support surface e.g., planar or cylindrical is provided, and the intervening layer is a drawn coating applied directly or indirectly to the rigid member in the direction of the straight surface, preferably drawn substantially according to FIG. 13, described below, preferably the intervening layer comprising colloidal silica or a soluble silicate.

A surface of one of the constituents of the device, prior to being united with a next constituent layer of the device, is in a surface-treated state for enhanced adhesion of that surface to the next constituent layer.

An intervening layer is at least partially opaque, the intervening layer blocking at least 30%, preferably blocking at least 50%, or often preferably blocking at least 70% of incident radiation at a wave length corresponding to the stimulating or emission wavelength of a fluorophore or luminescent tag on biological material.

The rigid support has characteristic fluorescence or luminescence in response to incident stimulating radiation, an intervening layer being effective to at least substantially limit penetration of incident stimulating radiation from the substrate layer to the support or limit penetration of fluorescent or luminescent radiation from the support to the substrate layer, or both.

The intervening layer is electrically conductive and an electric terminal may be associated with the intermediate layer for applying a voltage potential to the layer to promote binding or rejection of biological material exposed to the substrate layer.

The device may be constructed and arranged to support biological material for microscopy, and an intervening layer of an oxide of metal, preferably oxide of tantalum or aluminum, may be adapted to serve at least one of the functions, preferably more than one, of adhesively uniting, either directly or indirectly, the rigid support with the deposit-receiving substrate layer, of providing an opaque barrier to prevent or substantially limit light passing between the deposit-receiving substrate layer and the support, of providing a radiation-absorptive layer to heat the substrate layer, or of providing an electrically conductive layer as a means to heat, electrically charge, inspect, treat or excite the substrate layer.

The substrate layer is adapted to receive a deposit of biological material and to be temporarily engaged by an object adjacent the deposit, as by an elastomeric gasket, wherein the substrate layer is interrupted so that adherence of the substrate to the object does not disrupt the array when removing the object, preferably an intervening adhesion promoting layer beneath the substrate layer being interrupted such that a substrate layer applied thereto is disrupted, for example by a moat, formed by a gap in a pattern of a metal oxide adhesion promoting intervening layer, in some cases the substrate layer being applied as a continuous fluid coating which separates on drying at interruptions of an adhesion promoting layer, such as the metal oxide layer.

For use in microscopy, an outer surface of the substrate layer is constructed to receive deposits of biological material thereon in position exposed for direct illumination and inspection from the exterior.

In some cases, devices according to the invention are functionally at least partially transparent to pass effective light in at least one direction between a deposit on the substrate layer and through the rigid support, as in the case of multiwell plates. For instance the device may be arranged to enable illumination of a deposit of biological material on the substrate layer via the rigid support, or the device may be arranged to enable microscopic inspection of a deposit of biological material on the substrate layer via the rigid support, or the device may be arranged to enable microscopic inspection from both the exterior side of the substrate layer side and via the rigid support.

According to another aspect of the invention, a device for immobilizing biological material is provided comprising a polymer substrate layer having biological immobilizing properties, preferably for protein or nucleic acid, the substrate layer deposited on a rigid support, and having an outer deposit-receiving region exposed to receive biological material, wherein the rigid support defines a straight support surface e.g., planar or cylindrical, and the substrate layer is a drawn coating applied directly or indirectly to the rigid member in the direction of the straight surface, preferably drawn substantially according to FIG. 14 to be described below, preferably there being at least one intervening layer, which lies between the rigid support and the ultra-thin polymer substrate layer, the intervening layer adherently joined on each of its oppositely directed faces to substance of the device and preferably used where immediately adjacent materials on opposite sides of the intervening layer are not as adhesively compatible with each other as each is with the intervening layer.

According to another aspect of the invention, a device for immobilizing biological material is provided comprising a polymer substrate layer having biological immobilizing properties, preferably for protein or nucleic acid, the substrate layer deposited on a rigid support, and having an outer deposit-receiving region exposed to receive biological material, wherein at least one intervening layer lies between the rigid support and the polymer substrate layer, the intervening layer adherently joined to substance of the device on each of its oppositely directed faces, and the intervening layer is at least partially opaque to radiation employed to stimulate emission from the biological material, the layer limiting or preventing transmission of radiation from the rigid support, used preferably in cases in which immediately adjacent materials on opposite sides of the intervening layer are not as adhesively compatible with each other as each is with the intervening layer.

According to another aspect of the invention, a device for immobilizing biological material is provided comprising a polymer substrate layer having biological immobilizing properties, preferably for protein or nucleic acid, the substrate layer deposited on a rigid support, and having an outer deposit-receiving region exposed to receive biological material, wherein at least one intervening layer lies between the rigid support and the polymer substrate layer, the intervening layer adherently joined to substance of the device on each of its oppositely directed faces, preferably used where immediately adjacent materials on opposite sides of the intervening layer are not as adhesively compatible with each other as each is with the intervening layer, and wherein an intervening layer comprises an electrically conductive layer, for instance, the electrically conductive layer being associated with at least one electrical terminal and the conductive layer and the electrical terminal are constructed and arranged to provide a voltage potential to the receiving surface of the device to promote binding or rejection of material exposed to the outer deposit-receiving surface of the substrate layer.

In such cases involving intervening layers, preferably one or more layers of the device is in a surface-treated state for enhanced adhesion to an overlying layer or for adhesion of deposits of biological material thereon, for example the surface treatment being that provided by a corona treater.

One or more of the following novel features is useful with each of the various aspects of the invention that have been described.

The substrate layer is substantially solid, preferably having a thickness less than about 5 micron, preferably less than 3, 2 or 1 micron and in preferred embodiments between about 0.1 and 0.5 micron.

The substrate layer, at least in its outer region, is micro-porous, preferably the substrate layer being micro-porous throughout its thickness, and preferably, the substrate layer having a thickness less than 3 micron, preferably less than 2 or 1 micron.

The substrate layer is nitrocellulose or polystyrene, preferably residing on an intervening surface adhesion promoter layer, preferably that intervening layer comprising an adherent oxide of metal, preferably tantalum or aluminum oxide, or comprising colloidal silica or a soluble silicate that is preferably a drawn coating.

More broadly the substrate layer is selected from the group consisting of nitrocellulose, polystyrene, cellulose acetate, cellulose triacetate, ethyl cellulose, activated nylon, polytetrafluoroethylene (PTFE), polyvinyl difluoride (PVDF), polyamide, polyvinylchloride (PVC), divinyl benzene, and agarose.

A surface-treated state of the substrate of an intervening layer is the result of exposure of the respective surface to corona or flame treatment, bombardment with charged particles including electrons, ions, and sub-atomic particles, or exposure to electromagnetic radiation, such as ultraviolet, gamma, or X-ray wavelengths.

The rigid support is a microscope slide, preferably a frosted microscope slide, preferably a blank frosted glass slide, preferably the microscope slide being coated with a metal oxide, or has an adhered drawn coating, as by the process shown in FIG. 13, described below, or both, or the device is in the form of a bio-cassette, a CD disk, the bottom of a multi-well plate, or a hollow tube.

A multiwell plate comprises an upper well-defining structure and a bottom plate comprising a substrate layer, the upper well-defining structure and the upper surface of the bottom plate member being of dissimilar material, and an adhesion promoting intervening layer being disposed between the upper well-defining structure and the bottom plate, the well-defining structure being polystyrene or similar polymer and the support of the plate member being glass, fused quartz, silicon or ceramic, the adhesion promoting layer preferably comprising an adherent metal oxide, e.g., tantalum oxide or aluminum oxide, and preferably a layer of polystyrene or similar compatible polymer being disposed over the adhesion promoting layer to which the well-defining structure is bonded.

A localized reference deposit of stable fluorescent material is provided on the device, preferably characterized by a broad fluorescence spectrum, e.g. polyimide, and preferably disposed on the device in position to be read by an optical instrument such as a microscope or CCD sensor for quality control of production of the device, or as an intensity calibrator during reading of fluorescence of substance deposited on the substrate layer.

The support is selected from the group consisting of glass, fused quartz, silicon, plastic, PMMA or polystyrene, or where not requiring transparency, of ceramic or a metal such as gold, aluminum or silver.

The outer surface of the substrate layer is generally flat and arranged to receive the deposit of a spotted array of bio-material, or already carries an array of bio-material spots either in unreacted state or in a reacted state as a result of performance of an assay in which at least some of the said spots carry a fluorescent label.

According to another aspect of the invention, a method is provided of forming the device including applying directly or indirectly to the rigid support a fluid containing the polymer of the substrate layer under conditions to form the substrate layer, preferably by drawing the rigid support from a bath of coating composition, preferably this including applying an adhesion-promoting layer directly or indirectly to the rigid support before application of the substrate layer, preferably by applying a metal, preferably tantalum or aluminum and allowing it to oxidize, or applying soluble silica or colloidal silicate by drawing from a bath. In these cases, preferably forming conditions are maintained to produce a solid film coating as the substrate layer, or are maintained to produce a micro-porous substrate layer.

The methods preferably include post-treating the substrate layer coating to alter its structure or properties, for instance subjecting the coating to corona discharge or to reactive gas or to structure-changing radiation, or to a combination of solvents selected to form pores.

The substrate layer is formed of nitrocellulose or polystyrene.

An opaque layer is applied directly or indirectly to the rigid support before applying the substrate layer, for instance a metal oxide layer is applied of sufficient thickness as to be at least partially opaque, to serve as a barrier to transmission of radiation.

One or more surfaces is treated during forming of the device by increasing surface energy, or altering the surface structure, or affecting biological binding affinity in the case of a receiving surface for a molecule or bio-material of interest or of a material wished to be rejected, for instance subjecting the surface to corona or flame treatment, or bombardment with ions or sub-atomic particles, or exposing the surface to selected electromagnetic radiation such as gamma radiation or X-rays.

In a commercial manufacturing process for production of a support film for spotted biological specimens for reaction or analysis and fluorescence measurements for quality assurance, the step of measuring fluorescence in response to excitation of the support with a wavelength intended to be used with the biological specimen, preferably the process parameters being selected to produce a coating having a fluorescence level of no more than about five times, preferably no more than about three times, or two times the fluorescence obtained from the uncoated rigid member.

For producing a substrate support for spotted biological specimens for reaction or analysis, performing the steps comprising: (a) at least partially immersing a rigid member that defines a straight support surface (e.g., planar or cylindrical) in a vat containing a coating solution comprising a biologically compatible organic film-forming composition which includes at least one volatile solvent, (b) progressively drawing the member from the solution along a fixed path into a still environment, (c) the fixed path being generally parallel to the straight support surface, (d) the conditions of the still environment enabling the solvent to evaporate to leave a drawn coating of the composition adhered to the support surface, for example the rigid member being a microscope slide, or a component of a bio-cassette, or the bottom member of a multiwell plate and the conditions being maintained to cause the formation of a solid film, e.g. a thin film of polystyrene or nitrocellulose, for example the film-forming composition comprising nitrocellulose dissolved in amyl acetate or an organic solvent such as acetone, dimethylsulfoxide, ethyl acetate, or other common organic solvents or the organic film-forming composition comprising polystyrene dissolved in an organic solvent such as acetone, dimethylsulfoxide, ethyl acetate, or other common organic solvents, or the method being conducted to produce a micro-porous membrane, such as a nitrocellulose micro-porous membrane, as by dissolving nitrocellulose in methyl acetate, ethyl alcohol, butyl alcohol, water, and glycerol.

Providing the support in the form of a disc having an adherent surface for a substrate coating fluid, spinning the disc individually, preferably the disc being in the form of a compact disc (CD), and providing a substrate coating fluid in the center region of the disc while it is spinning, to enable radial distribution of the fluid and removal of all except that retainable by action of surface forces.

Another aspect of the invention is a method of conducting an assay including providing a device according to any of the above description or by the methods of the above description, applying an array of spots of bio-material to the substrate, conducting an assay which tags at least some of the spots with a fluorescent or luminescent label, and, after washing the array, reading the array by fluorescent or luminescent detection, preferably the assay being based on protein-protein interaction, or involving an array comprising nucleic acid or other genetic material, or comprising viruses, peptides, antibodies, receptors, cDNA clones, DNA probes, oligonucleotides including synthetic oligonucleotides, or polymerase chain reaction (PCR) products, or the array comprising plant, animal, human, fungal or bacterial cells, or malignant cells, or cells from biopsy tissue. Preferably the reading is accomplished with a CCD sensor, preferably accomplished by the dark field reflection mode.

DESCRIPTION OF DRAWINGS

FIG. 9 illustrates diagrammatically laser ablation of a microscope slide to produce a marking on its surface, while

FIG. 15 illustrates microscope slides being withdrawn from a polymer composition for applying a drawn ultra-thin substrate film while FIG. 16 illustrates the dried substrate;

FIGS. 17 and 18 similarly illustrate forming a drawn microporous membrane. Note that the microscope slide thickness in each figure has been broken away to suggest the relatively small thickness of the applied coatings.

FIG. 21 is a diagrammatic perspective view of a bio-cassette having a protein microarray on an ultra-thin membrane, e.g., for supply to clinical laboratories for patient diagnosis, while

FIG. 23 is a diagrammatic plan view, on an enlarged scale, of an array of protein spots on a substrate layer, surrounded by a moat in the substrate layer, while FIG. 24A is a diagrammatic plan view of a portion of a microscope slide showing four such micro arrays, FIG. 24B is a diagrammatic transverse cross-sectional view taken on line 24B-24B of FIG. 24A, and FIG. 24C is a highly magnified view of a portion of FIG. 24B.

FIG. 24D is a view similar to FIG. 24A with a gasket in place and FIG. 24E is a similar view with the gasket removed and by a circle, showing the field of view of a microscope inspecting the slide.

FIG. 31 is a view similar to FIG. 30 of an alternative construction while

FIGS. 32 and 33 are cross-sectional views of two parts of a multi-well plate prior to assembly of another construction while

Like reference symbols in the various drawings indicate like elements. All percentages given in the formulations are by weight.

DETAILED DESCRIPTION

Figure 1:
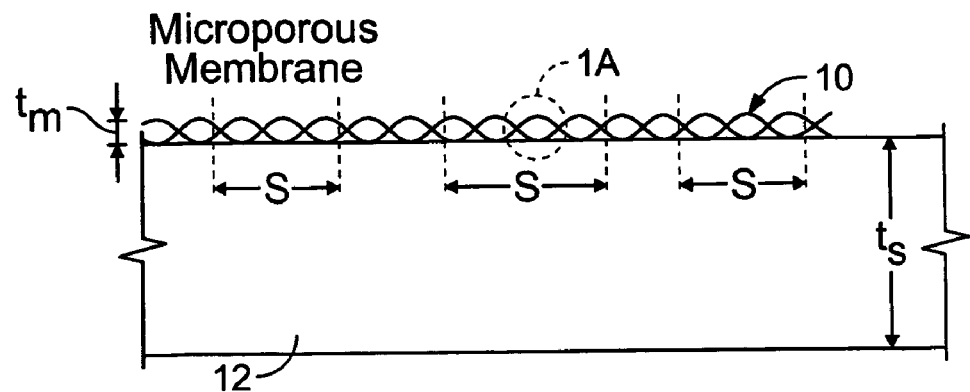
FIGS. 1, 1A and 1B, in three stages of increasing magnification, are diagrammatic cross sections of a porous polymeric membrane of the prior art showing a possible distribution of biological material relative to the volume of the porous structure of the membrane.

Referring to prior art FIG. 1, a conventional membrane 10 of nitrocellulose of thickness $t_m$ of e.g. 12 to 15 micron is diagrammatically depicted upon the surface of a transparent, rigid support 12, e.g. a glass microscope slide of thickness $t_s$ of e.g. 1 mm.

Figure 1A:
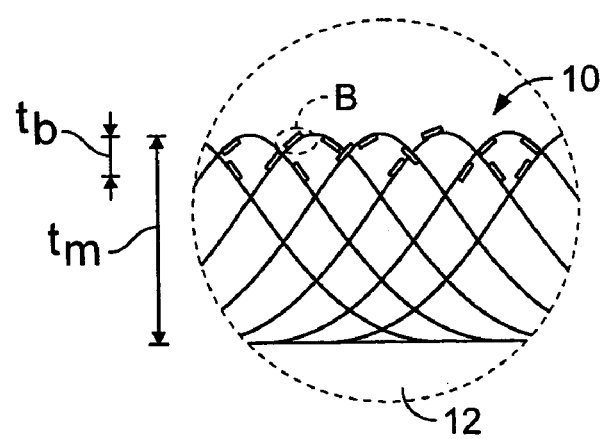

As suggested in the highly magnified diagram of FIG. 1A, the nitrocellulose layer of thickness $t_m$ is micro-porous in nature. Into its interstices, to a limited depth $t_b$, biological material B of a deposit is shown to have migrated as the result of a spotting or other deposit technique. Typically the biological material B, deposited in a liquid suspension, migrates downwardly as the liquid is absorbed or progresses through the thickness of the membrane 10. The molecules of biological material bind to sites on the elements 10a of the substrate, see FIG. 1B, and are immobilized, while the carrier liquid disperses and evaporates. The depth of penetration $t_b$ of significant concentrations of biological material B depends upon factors such as degree of porosity of the nitrocellulose or other immobilizing membrane, size and configuration of the specific bio-material molecules in the suspension, overall viscosity of the liquid suspension, and method of deposit. In many spotted arrays of the prior art, depth of penetration $t_b$ of molecules B is substantially less than the overall thickness $t_m$ of the membrane, typically substantially less than half. For instance, with a conventional nitrocellulose membrane of thickness $t_m$ of 12 to 15 micron, the depth of penetration $t_b$ of significant quantities of the biological molecules is often of the order of one third or less than the thickness $t_m$, e.g. $t_b$ is equal to 3 or 4 micron, though penetrations up to 6 or 7 micron at other times may be observed.

Figure 1B:
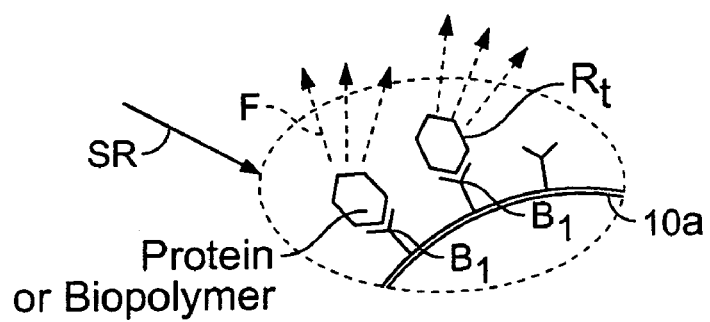

As depicted in FIG. 1B, immobilized molecules $B_1$ reside on the surface of a constituent element 10a of the micro-porous membrane. During assay of the spotted array, a fluorescently or luminescently tagged molecule of reagent $R_t$ binds to molecule $B_1$. When excited by stimulating radiation SR to fluoresce or luminescence, it emits radiation F, of wave length characteristic of the tag.

Figure 2:
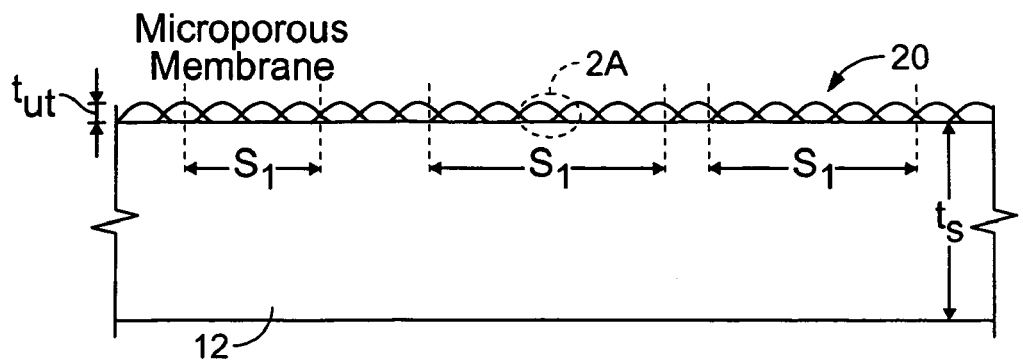
FIGS. 2 and 2A are, in two stages of increasing magnification, cross sections, similar in type, respectively, to FIGS. 1 and 1A, of an ultra-thin micro-porous bio-material-immobilizing polymer membrane embodiment of the invention, showing a possible distribution of biological material within the porous ultra-thin coating.
Figure 2A:
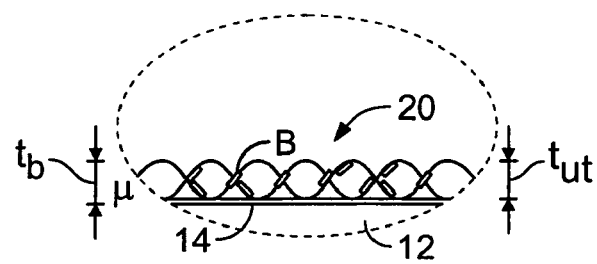

Referring to the embodiment of FIGS. 2 and 2A of the present invention, an ultra-thin micro-porous immobilizing membrane 20, of thickness $t_{ut}$, e.g., of e.g. 2 to 3 micron, is coated upon the support 12, which again may be a glass microscope slide. Adhesion of the ultra-thin layer is enhanced by an intervening adhesion-promoting layer 14. Layer 14 may be, in the case of a glass support, silane or epoxy-silane (which offers a covalent bond to nitrocellulose and consequently is able to support a mono-layer of nitrocellulose molecules), or other common surface adhesion promoters such as PEI (Polyethylene imine), and GAP (gamma amino propylene).

Preferably, however a layer of soluble silicate such as sodium silicate or colloidal silica, or a thin oxide of metal layer, such as of tantalum oxide or aluminum oxide, is employed or in some preferred cases, successive layers of one from each of these groups is employed.

As depicted in FIG. 2A, as a result of deposit by spotting, significant quantities of the biological material B penetrate to a depth $t_b$ equal to the majority of the thickness of the immobilizing membrane 20, preferably to more than two thirds of the thickness, or, as depicted in FIG. 2A, substantially through all of the 2 to 3 micron thickness $t_{ut}$ of the ultra-thin micro-porous membrane.

Comparison of prior art FIGS. 1 and 1A with the embodiment of FIGS. 2 and 2A, illustrates advantages of the invention. For the comparison, we assume that the specific density and microscopic structure of the prior art membrane 10 of thickness $t_m$ of, say 12 micron, is the same as the microscopic structure of the ultra-thin membrane 20 of thickness $t_{ut}$ of FIGS. 2 and 2A. Also, we assume for purposes of discussion, a penetration depth $t_b$ of 3 micron of the biological material in both FIG. 1A and FIG. 2A, with the same number of bio-molecules being immobilized in the same distribution in each case. According to principles already explained, the fluorescent signal attributable to the tagged molecules will be equal in the two cases, but, because the volume of the nitrocellulose or other immobilizing substrate material, per unit area of FIG. 1A, is about four times greater than the volume per unit area of FIG. 2A, the self-fluorescent noise signal from the nitrocellulose or other immobilizing material will be significantly greater with the conventional prior art membrane of FIG. 1A. Even if the subtraction correction is employed, such correction is never perfect, the error generally being proportional to the size of the original error signal. Thus, improvement in corrected signal is obtainable with the embodiment of FIGS. 2 and 2A.

Other factors may result in even greater improvement by use of the ultra-thin layer. Assume a suspension of biological material in a spot quantity has a tendency to penetrate deeper than the depth $t_b$ of 3 micron depicted in FIG. 1A. In the case of FIG. 1A, some of the molecules penetrate deeper, and those deeper molecules receive less excitation due to their greater depth and suffer loss of their fluorescent signal as the radiation makes its way back to the surface through the diffusive porous medium. This detrimentally affects the signal-to-noise ratio.

The continuous ultra-thin membrane of the embodiment of FIGS. 2 and 2A is found to retain a key attribute of conventional much thicker nitrocellulose membranes of the prior art, that of enabling imaging the unoccupied membrane between spots to enable subtraction of a value representing detrimental background fluorescence. Therefore, it is seen that the embodiment of FIGS. 2 and 2A has significant advantages over the spotted mixture approach recently proposed by Pinkel and by Audeh, et al., referred to earlier.

Figure 3:
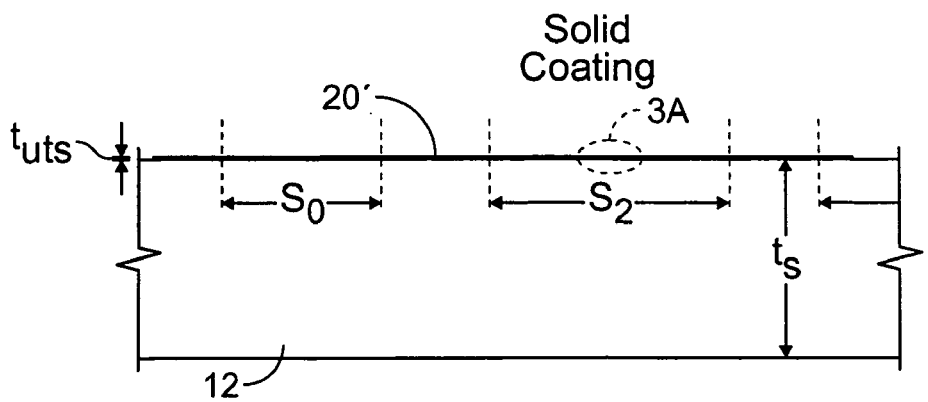
FIGS. 3 and 3A are views similar to FIGS. 2 and 2A, respectively, of an ultra-thin solid bio-polymer-immobilizing polymer membrane.
Figure 3A:
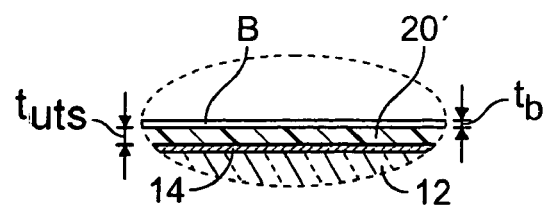

Referring now to FIGS. 3 and 3A, in this embodiment a solid ultra-thin film of immobilizing substrate material 20' is formed by the techniques mentioned. Upon an adhesion promoting layer 14 on the support 12, an ultra-thin solid coating 20' of nitrocellulose or other protein-immobilizing polymer substrate material is formed of a thickness $t_{uts}$ of e.g. 0.1 to 0.5 micron. The resultant membrane, being solid, i.e., substantially non porous, as well as being continuous in X, Y extent, presents a superficially planar array-receiving surface (albeit, as with any surface, the surface exhibits microscopic or submicroscopic roughness over which the binding sites of the material are distributed.)

At a first order of approximation, all binding sites of this generally planar surface are exposed for binding of the biological material. Substantially no binding sites are in the shade of over-lying immobilizing material. For reasons explained above, this arrangement provides more of what may be called "first order" binding sites, and hence permits highly efficient use of the biological material, should it be in short supply, as well as efficient use of reagents that may be expensive and in small quantity.

As with the embodiment of FIGS. 2 and 2A, the embodiment of FIGS. 3 and 3A, also permits subtraction of background signal, and hence can represent a significant advantage over the Pinkel and Audeh et al., approach, as well as significant advantage over prior commercially available substrates.

It is important to note that the substance of the ultra-thin substrate layer in both FIGS. 2 and 3 is nitrocellulose suitable for immobilizing protein molecules such as viruses, peptides, antibodies, receptors, and other proteins or to a wide range of biological materials including, plant, animal, human, fungal and bacteria cell, cDNA, DNA probes, oligonucleotides, polymerase chain reactions (PCR) products, and chemicals. An ultra-thin substrate layer of polystyrene, according to the invention, is also particularly effective for such biological materials.

Figure 4:
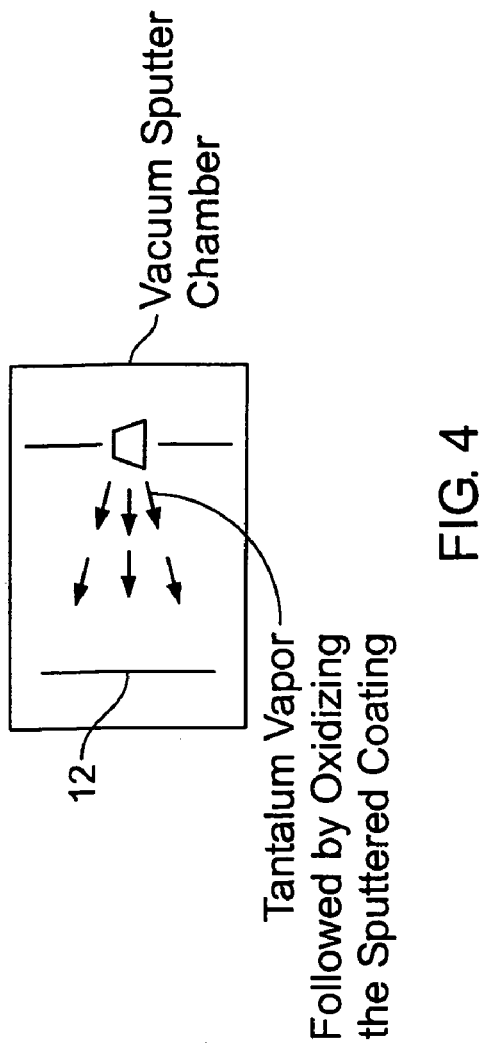
FIG. 4 is a diagram illustrating vacuum deposition of metal onto a microscope slide.

In forming the devices of FIGS. 2 and 3, prior to applying the ultra-thin layer, as shown in FIG. 4, glass slides 12 are exposed to vapor deposit conditions or sputter coating conditions for application of a metal-based coating, e.g., tantalum, which oxidizes to form tantalum oxide, or aluminum, which oxidizes to form aluminum oxide.

The metal for the oxide coating applied e.g. by sputter coating can be of Angstrom range thickness. By a simple protocol of optical transmission measurements of resultant layers over a coating series of changed duration, the metallizing conditions are determined according to the desired degree of transmissivity or opacity desired. Similar techniques are common in the design and production of optical coatings, to which reference is made. For present purposes, it has been shown that coatings 54 of tantalum, converted to tantalum oxide, that permit 90% transmission to almost no transmission have effective adhesion qualities for instance, to glass, to serve as the support 12, as well as to nitrocellulose and polystyrene, desirable materials for the biocompatible substrate 56. At 70% transmission (blocking 30%) or less, e.g. 50% (blocking 50%) or 30% transmission (blocking 70%), an angstrom range thickness layer is effective to reduce or substantially eliminate from sensing in reflective mode, any fluorescence, luminescence or stray radiation that may originate in or enter through the substance of a glass microscope slide or other transparent, rigid support.

After application of such an oxide layer, or other adhesion promoting layer such as described below, or combination of such layers, the slides are stored in a controlled dry environment at room temperature, ready for the next step.

The coatings described above ensure proper adhesion of the nitrocellulose or other ultra-thin immobilizing substrate polymer to the glass support 12. A number of other adhesion promoters can also be used, sodium silicate or colloidal silica presently being preferred among the alternatives.

Also, microscope slides coated with other adhesion promoters may be purchased from commercial houses such as Erie Scientific.

Figure 5:
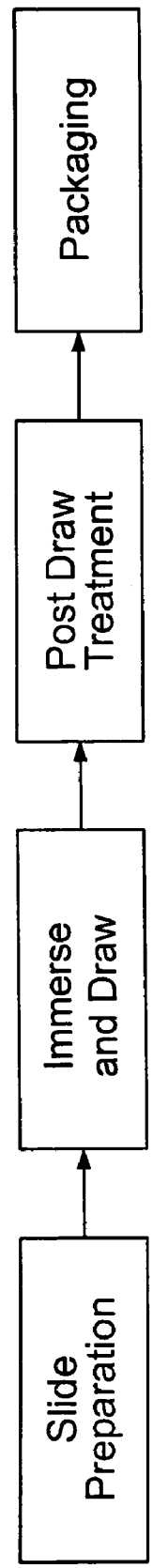
FIG. 5 is a general work flow diagram of manufacturing thin film coated microscope slides.

According to a feature of the invention, an advantageous method of preparing thin-film or microporous membrane coated slides employs drawing slides from immersion in a polymeric solution. Generalized steps for the method are shown in FIG. 5. Slides are prepared prior to immersion, are immersed and drawn from a polymeric solution, which is then followed in many advantageous cases by a post drawing surface treatment such as exposure to corona discharge, etc. As previously noted, the resultant coating is referred to herein as a "drawn" coating.

The slide preparation can advantageously employ steps of applying one or more layers of adherence promoting layers and, as well, may employ surface treating the surface of the base support or one or more of the added layers to promote adhesion of the next layer.

Figure 6:
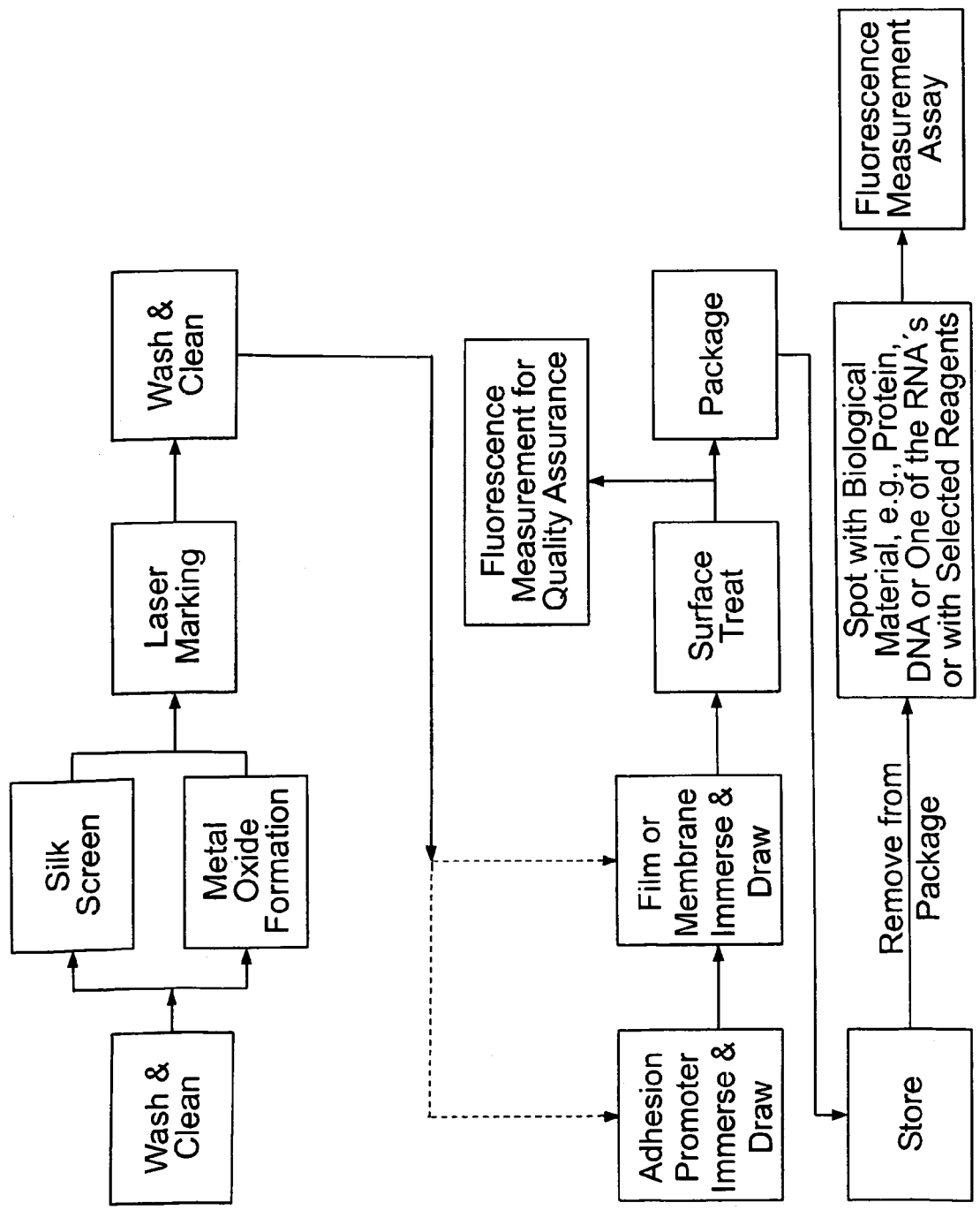
FIG. 6 shows a typical sequence of operations to coat slides. Dashed lines represent alternative steps.

FIG. 6 illustrates the succession of preferred steps (with preferred alternatives) in a method used to prepare commercial glass slides for protein or nucleic acid processing. Alternative steps are indicated by dashed line in FIG. 6. For example, after the initial wash and clean step, a slide is silk screened or coated with tantalum oxide, in preparation for marking and serialization.

Figure 7A:
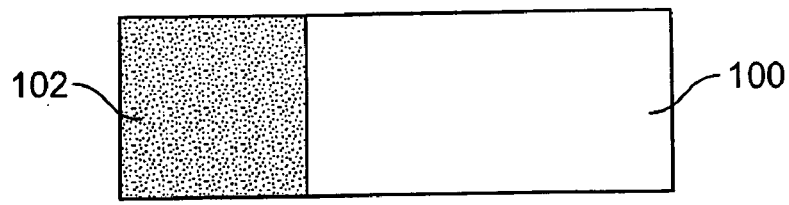
FIGS. 7A and 7B show two frosted microscope slides; the frosted slide in 7B bears silk screen printing over the frosted area and over a thin border region surrounding the spotted array-receiving area.
Figure 7B:
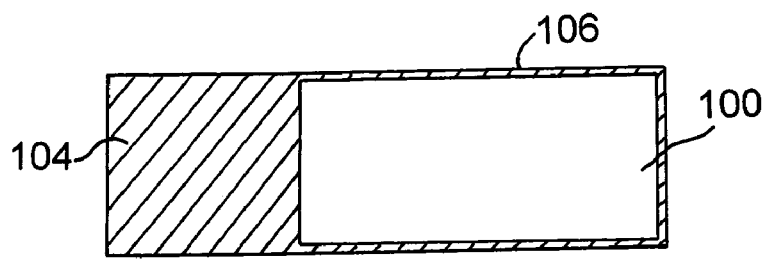

Referring to FIGS. 7A and 7B, a silk-screened pattern 104 is applied. It covers the frosted side 102 of the slide 100 as well as providing any frame 106 that may be desired. A frame, tracing the outer periphery of the slide, may have a width of 1 to 3 mm (preferably 2 mm). The region over the frosted end 102 may be marked and serialized e.g. with a commercial laser marker. The peripheral frame may serve both for protection and aesthetic purposes.

Figure 8:
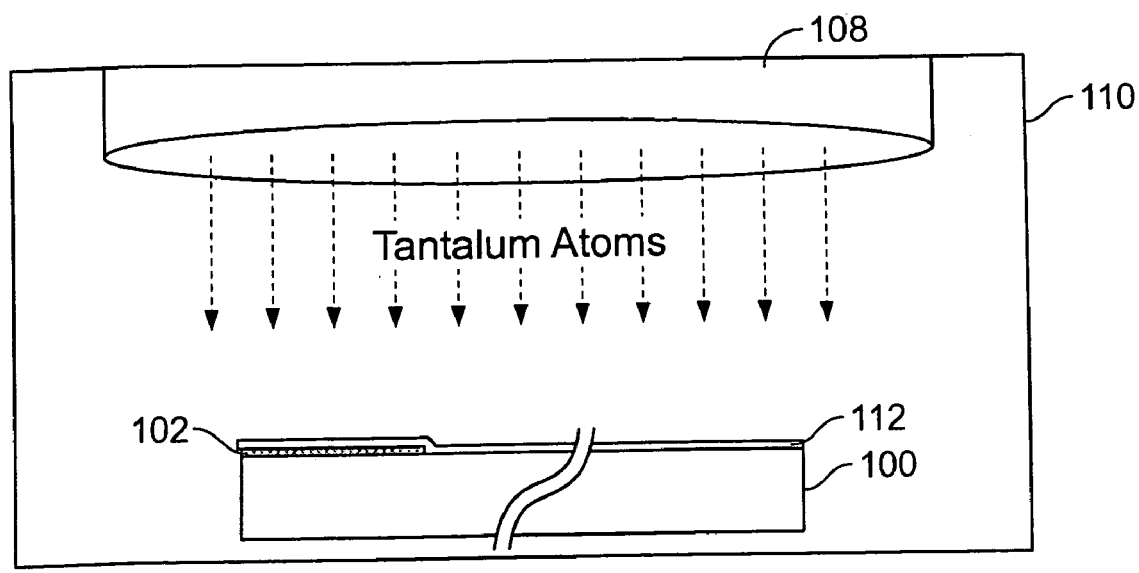
FIG. 8 diagrammatically illustrates coating a slide with tantalum from a source in a vacuum chamber, to be followed by oxide formation.

Referring to FIG. 8, alternatively, or in addition, a uniform metal coating 112, e.g. of tantalum oxide, is applied by sputtering or vapor depositing atoms from a source 108 onto the slide 100 in a vacuum chamber 110. This is followed by air oxidation. The oxide coating thus prepared is preferably at least partially opaque and employed to permit laser marking and serialization, as well as serving as an efficient adhesion promoter. Laser ablation may also serve advantageously to separate the region to be spotted into a number of separate sub-regions. The ablation may be performed on a coated substrate, or performed on an adherence promoting layer that leads to segmentation of a fluid-applied layer, as later described.

In important cases, using a transparent material for the rigid support, an opaque coating either the metal oxide, or other opaque layer, applied e.g. by printing techniques, blocks light transmission between the support and the biomaterial carrying substrate layer.

In embodiments when a transparent slide is desired, an oxide coating 112 is omitted or applied very thinly and the object is laser-marked at the silk-screen pattern 104.

Figure 9:
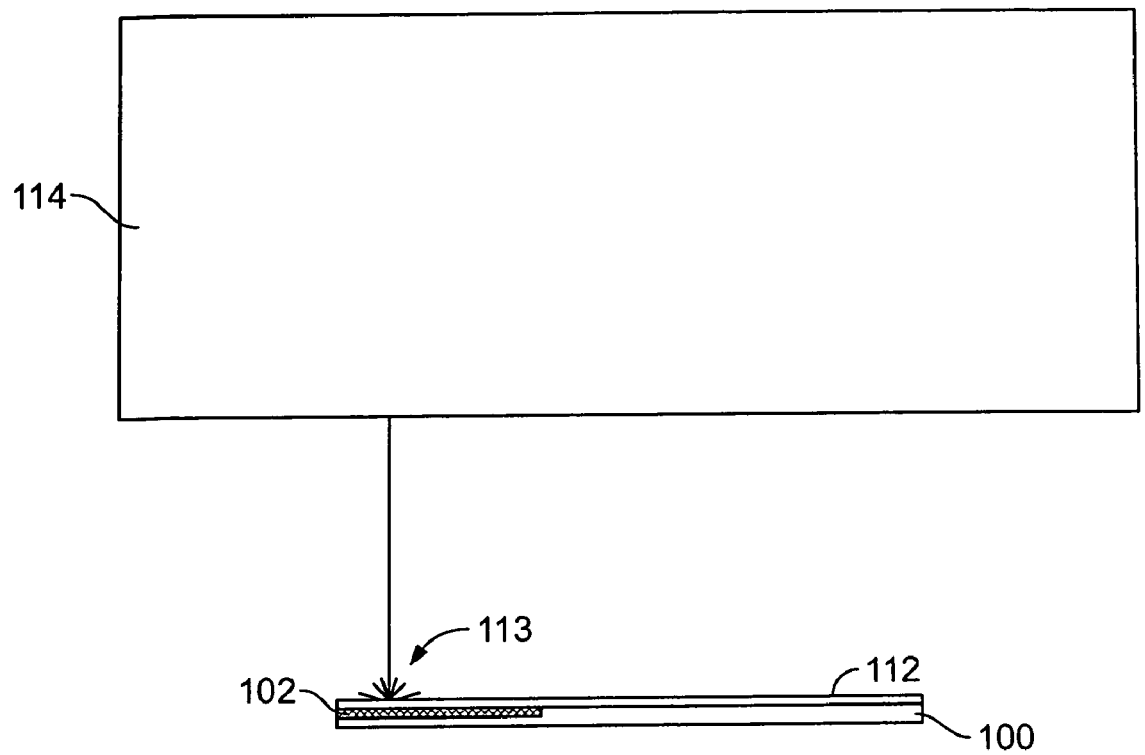
Figure 9A:
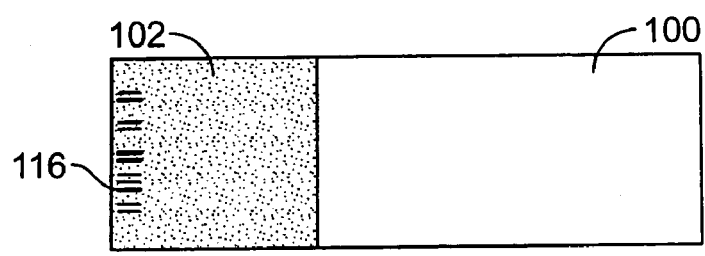
FIG. 9A is a plan view of the resultant slide.

FIG. 9 illustrates use of laser ablation 113 to mark the coating 112 over the frosted region 102 to serialize the slides 100 or add identification or registration markings 116 for automatic optical unit or information retrieval. Markings produced by laser ablation 113 may be used to enhance data acquisition reliability using various devices including, advantageously, commercial bar code readers.

After application of an adhesion promoting layer 112, one ore more durable sensitivity and geometry calibration spots may be locally deposited on slide 100. In a distribution such as suggested in FIGS. 11 and 23 reference spots may also be applied to the exterior surface of the substrate layer 20 or 20', here illustrated as in a pattern distributed across the array.

Reference spots, such as those at the corners of the array, may be employed as fiducial markings for geometrical reference, as by the imaging device. By suitable choice of materials such as the polyimide polymer mentioned, the same reference spots can serve as standards for the reading equipment to determine and accommodate long term variations in the optical instrumentation, such as light intensity or detector sensitivity. Likewise, they can be used to compensate for variation in illumination level over the area, e.g. to normalize the data across areas illuminated at different intensities.

Temporally stable spotting material such as polyimide (Kapton) may be used as the calibration spots, deposited in solution in a solvent using a commercially available spot printer. Preferably, the calibration compound is selected to have a broad fluorescence spectrum. These uses of reference spots are discussed further below with reference to the reader of FIG. 20.

Calibration markings 420 applied at the slide-manufacturing site, either below or on top of the substrate layer, can be employed in quality assurance steps whereby fluorescence of the ultra-thin film coated slides is measured following the final surface treatment step as indicated in FIG. 6. For quality assurance, fluorescence maybe measured from each unit or on a statistical sampling basis in accordance with quality control protocols.

Figure 12:
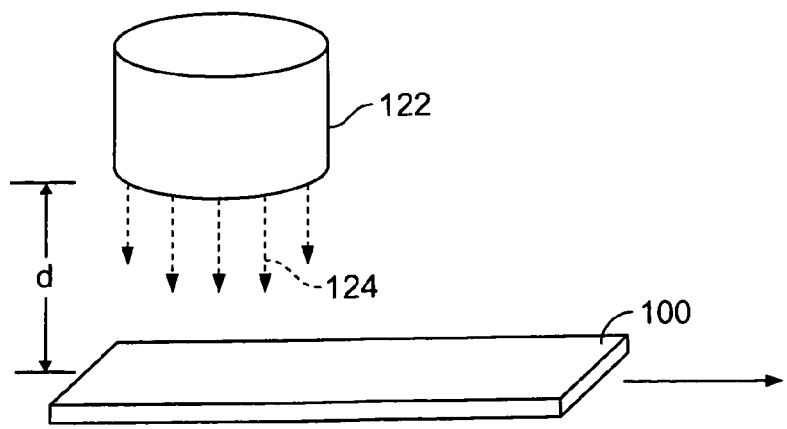
FIG. 12 shows diagrammatically a microscope slide undergoing corona treatment as it is translated.

Following the above steps, the slides are subsequently washed and, as shown in FIG. 12, exposed to surface treatment to promote adhesion properties of the film or membrane. During corona treatment, the slide 100 is translated under a jet of reactive species 124, e.g. ozone, produced by a corona treater 122 held at a distance d. If electromagnetic radiation such as ultraviolet light is utilized, a suitable source of photons is used to process the surface, e.g. a UV laser beam may be moved across the surface in suitable raster scan.

Figure 13:
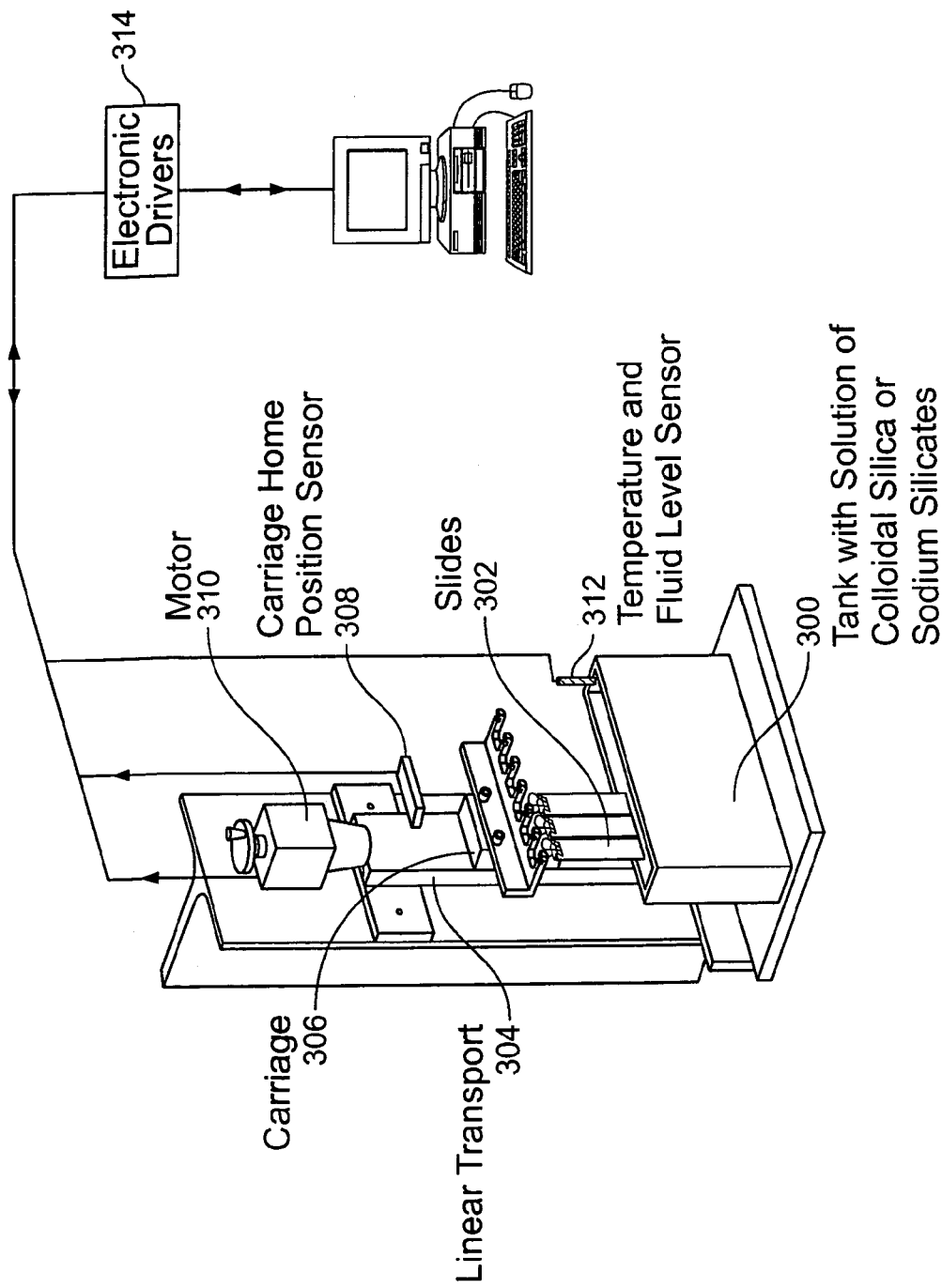
FIG. 13 shows a coating station at which a drawn film of colloidal silica or soluble silicate is applied to a glass microscope slide.

Referring to FIG. 13, immersion and drawing from a bath is employed for applying a layer to promote adhesion of the final substrate layer to be later applied. Drawing is preferably performed in a clean laboratory environment in a comfort humidity and temperature zone, preferably 33% humidity and 26° C. The cleaned and preferably recently (less than one day) corona treated slides 302 are immersed in a tank 300 of soluble silicate or colloidal silica, preferably a 3.3% solution of LUDOX CL from Sigma-Aldridge Co., and drawn out in the direction of the plane of the slide at a steady rate of approximately 0.5 in/min. The result is a coating of uniform thickness that serves as an adhesion promoting layer. (When not in use, the tank 300 should be closed to avoid evaporation, and the liquid should be stirred a minimum of once per day.)

Slides not coated with metal oxide preferably receive such a silica-based coating. Slides with a metal oxide deposit may or may not receive such a coating.

In preferred embodiments, a number of slides 302 are suspended from a rack and processed simultaneously to apply the silica-based coating. The group of slides attached to a carriage 306, such as a one-axis, vibration-free carriage linear-transport from Sherline Products in Vista, Calif., is translated, from the bath preferably at a uniform rate and between preset positions in a controlled manner. The slides thus coated with colloidal silica or silicate are air dried prior to being coated with the substrate layer material. The silica or silicate layer thus applied may be surface treated, e.g. according to FIG. 12, prior to application of the substrate layer.

Figure 14:
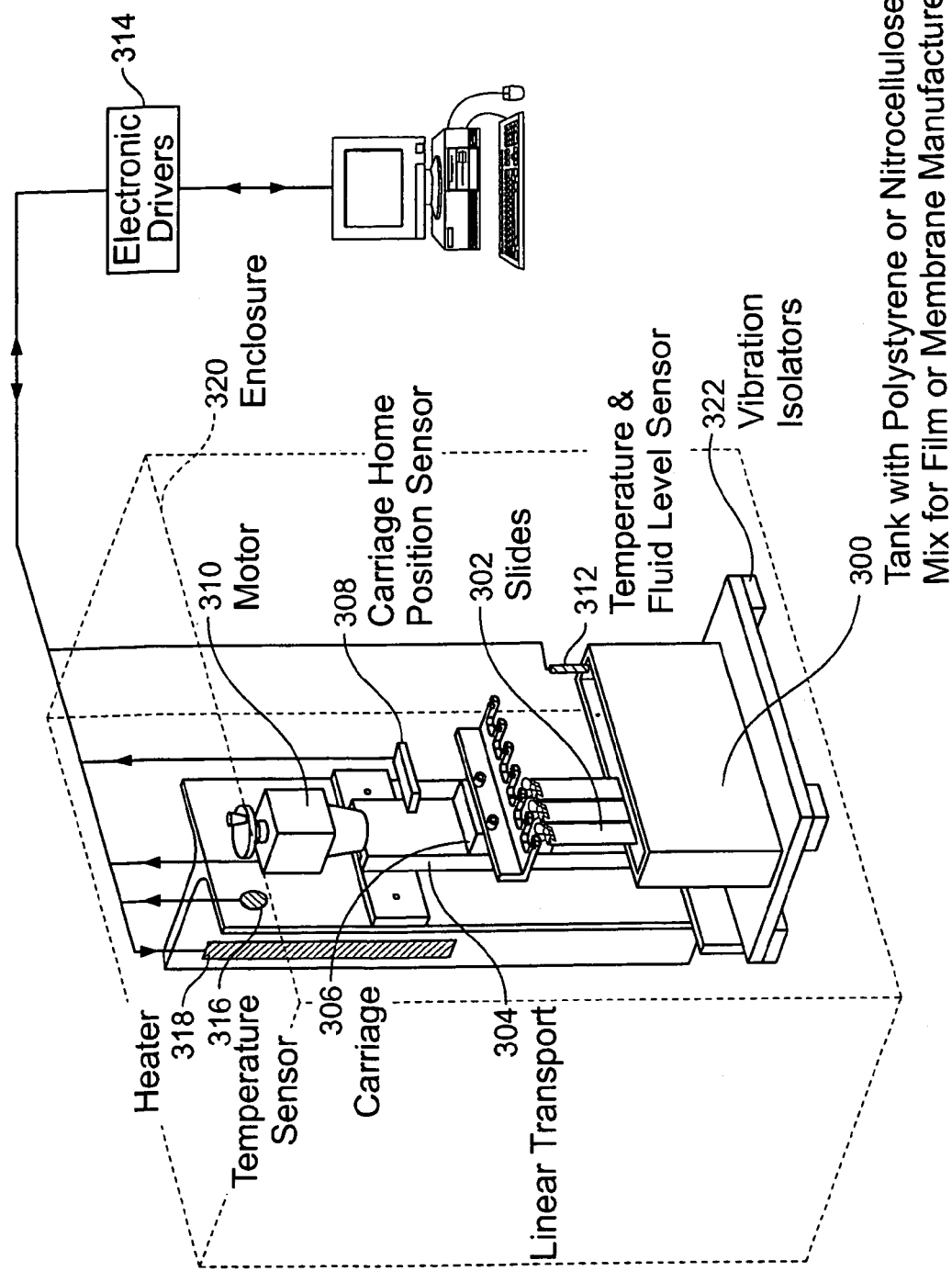
FIG. 14, similar to FIG. 13, shows a substrate coating station in which the tank holds a composition for producing a drawn film or membrane substrate layer on a microscope slide.

FIG. 14 shows a preferred embodiment of a coating station for application of the film or membrane substrate that is to receive the spotted array of biological material. The station is similar in construction and operation to the mechanism of FIG. 13. The process is performed in a still environment (i.e., substantially no air currents or vibrations), in vibration-free conditions, with control parameters of temperature, humidity, and draw rate selected in accordance with the purposes of the composition and the desired coating thickness. Slides are immersed, then drawn from the bath as indicated in FIG. 14. FIGS. 15-18 diagrammatically illustrate aspects of the drawing process as well as post-drawing features. Slides 900 are shown edgewise along their thinnest dimension t (typically about 1 mm for standard glass slides). FIGS. 15 and 17 represent drawing an immersed slide 900 respectively from a thin film coating composition 902 and a microporous membrane coating composition 904. During immersion, approximately ¾ of the length of a slide 900 is immersed in the polymer composition 902 or 904, i.e. the portion intended to receive the spotted array. As the slides 900 are drawn in translation direction represented by arrow 906, the polymeric compositions 902 and 904 adhere to the slides and form coatings 908 and 910 (stylized in the figures) on the surface of the slides 900.

As the slides are drawn and coated, the newly formed coating composed of polymer and solvent begins to dry. The initial thickness of the wet coating is shown diagrammatically in FIGS. 15 and 17, comprising the sum of the resultant film thickness, $t_f$ or $t_{mm}$, and thickness $t_v$ attributable to the volatile solvent. As solvent evaporates, the coating remaining on the slide surface becomes thinner and upon complete evaporation, $t_f$ is much thinner than $t_{mm}$ by several orders of magnitude, indicated diagrammatically in FIGS. 17 and 18.

Note the slide 900 is shown broken away in FIGS. 15-18 to emphasize the relative thinness of the film and microporous membrane structures.

In the case of interruption of the adherence promoting layers or treatment, the dried coating may form lines of discontinuities or separation moats for purposes to be described later in reference to FIGS. 23 and 24A-E, see especially moat M in FIG. 24C.

In these embodiments, following drawing and drying of the polymer coatings, the slides are subjected to surface modification with corona treatment (see FIG. 12) by translating the slide at a speed between 2 and 8 cm/min (preferably 4.4 cm/min) while maintaining the exposed surface to be treated normal and at a distance of between about 1 and 4 cm, (preferably 2 cm) from the jet of a standard 2.5 cm. round head of a corona treater, e.g. laboratory treater model BD-20AC from Electro-Technic Products Inc., of Chicago, Ill. operating near its optimal level.

The slides are transported between the various stations described by an operator or by suitable robots e.g. as part of standard commercial equipment or as part of a continuous production line.

Preferably, the coating process, including drawing the adherence-promoting layer and drawing the substrate film or membrane, as well as the post-drawing treatment, are performed in a clean room or within a hood.

The thus-formed substrate layers may also be subjected to other post forming treatments. For instance they may be treated to substrate-altering conditions, e.g. scanned under a laser or electron beam selected to provide porosity or otherwise to alter the overall bio-material binding characteristics or other structural features of the polymer membrane, such as for pore-forming with a laser or by an impinging fluid.

The slides, when completed, may be packaged as single units or in multiples (such as 5 or 20 slides).

After this preparation, the slides are ready to be spotted to form microarray A as shown in FIGS. 11, 19, 22 and 23. For instance the techniques explained in U.S. Pat. No. 6,269,846, which is hereby incorporated by reference in its entirety, may be used to form the array of spots 422. Simultaneously, according to a predetermined pattern, spots of reference material 420 may be strategically distributed throughout the array as suggested by FIGS. 10, 11, 22 and 23. Following this, the array is subjected to assay conditions, such as are generally described in the above-cited Chin et al., patent. After washing they are ready to be imaged.

Figure 20A:
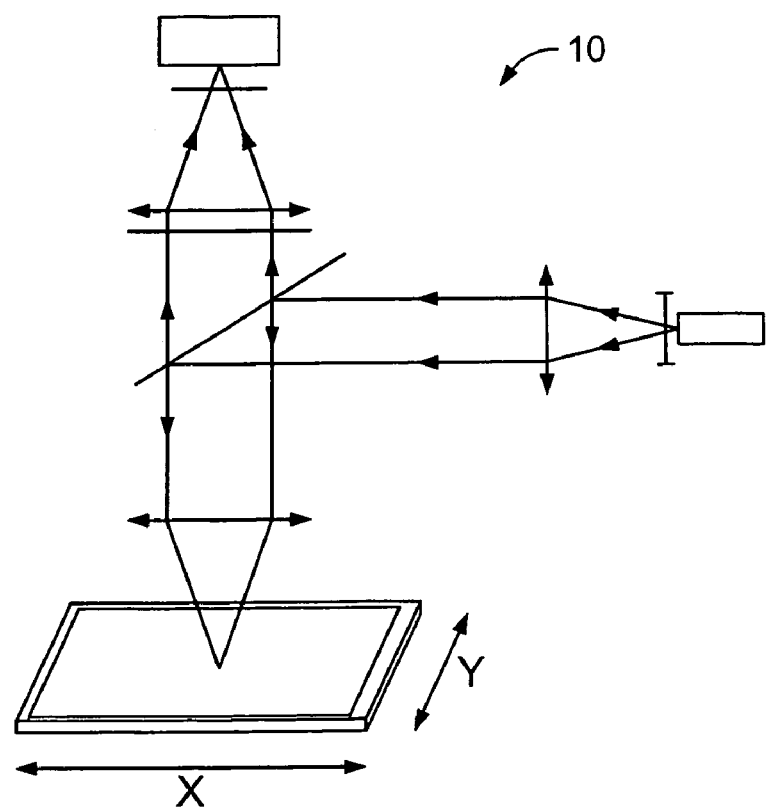
FIG. 20A illustrates imaging a spotted array on a solid ultra-thin bio-material-immobilizing polymer substrate, employing a confocal epi-microscope.
Figure 20:
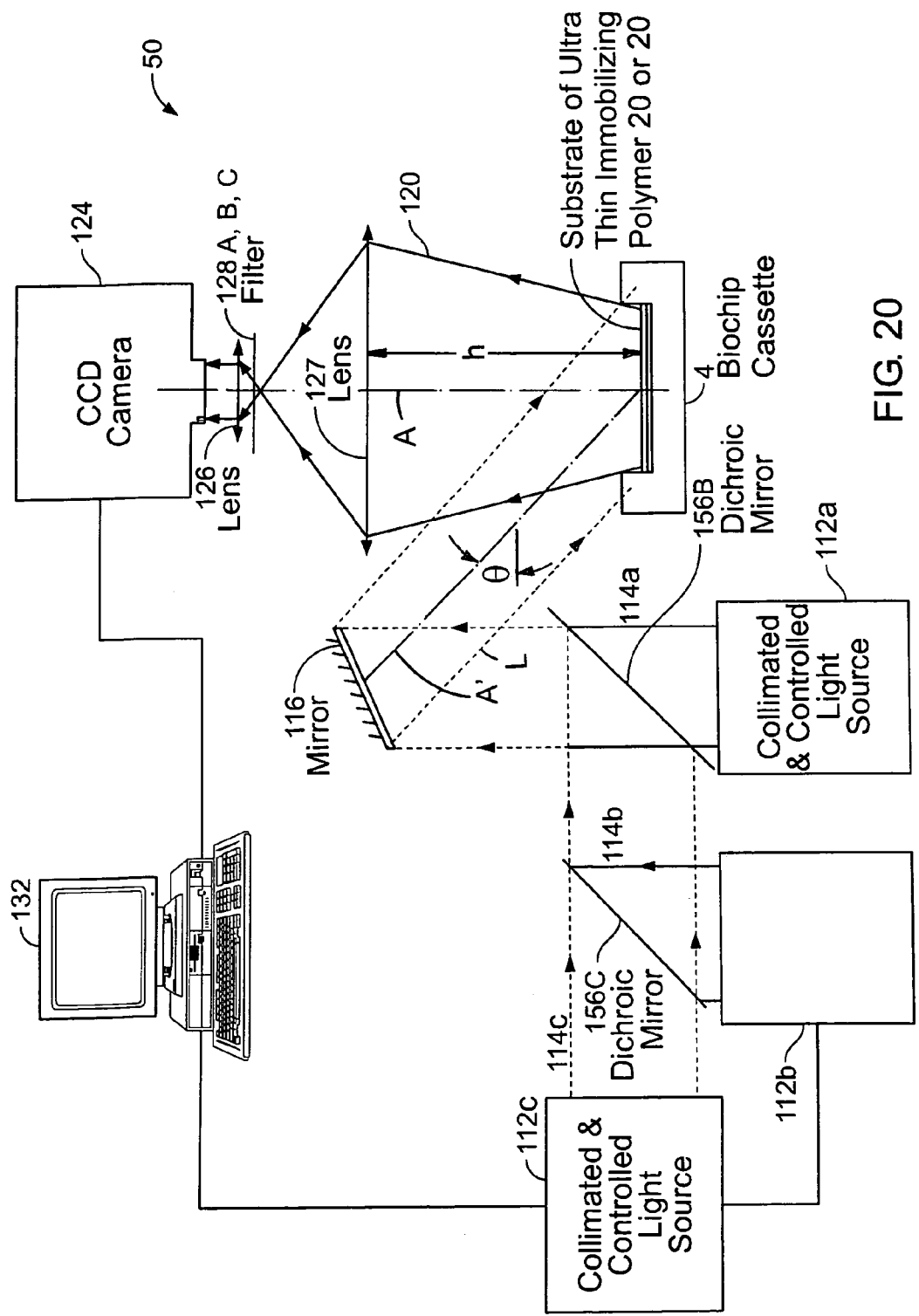
FIG. 20 illustrates fluorescent imaging, with a CCD sensor, by dark field reflection mode, of the spotted array resultant from the spotting of FIG. 19, employing a porous ultra-thin, immobilizing polymer substrate, after the array has been altered by an assay technique and suitably washed.

Referring to FIG. 20, imaging in a dark field reflectance mode may be accomplished with a CCD sensor 124 positioned to view the array along axis A normal to the plane of the array via collection optics 127, spaced a distance h from the substrate. In this case the substrate layer may be microporous partially or throughout its depth or may be a solid film or a modified solid film. As shown, light for direct illumination enters along an illumination axis A', at an acute angle θ to the plane of the array. Distance h must be selected to enable such direct illumination, with angle θ ranging between about 20° and 50°, here shown at 45°. Light L originates from a source 112a, 112b or 112c of wavelength selected to excite the fluorophore tag of the array, passes via dichroic mirrors 156b, 156c to mirror 116 located to the side that directs the illumination along axis A' at angle θ, onto the fluorophore-tagged array of spots resident on the ultra-thin substrate 20 or 20'. The fluorescent emissions are collected by lens 127, through a selected filter 128A, B or C, thence through lens 126 to CCD camera 124 under computer control 132. As before, the background subtraction technique is used with this system.

Referring to FIG. 20A, a confocal scanner imager 10 may also be employed. Such a confocal microscope may be constructed, for instance, according to Minsky, U.S. Pat. No. 3,013,467, or a scanning confocal microscope may be employed, such as the Affymetrix '428 Scanner, mentioned above. Such imagers may be in accordance with U.S. Pat. Nos. 6,185,030 and 6,335,824. The three patents of this paragraph are hereby incorporated by reference in their entireties.

For use in calibrating such imaging systems it is advantageous to provide the distribution of reference spots of known fluorescence in the array to be read.

Figure 10:
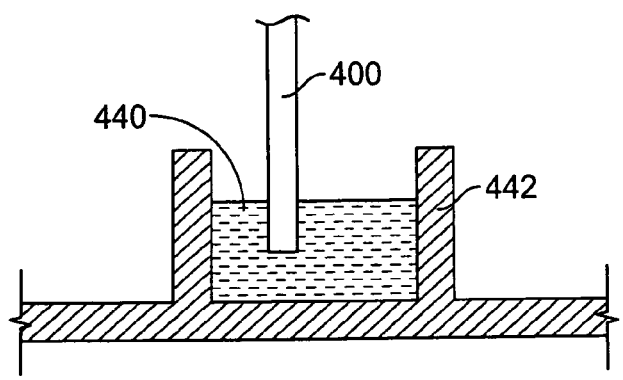
FIG. 10 depicts a well of a microwell plate containing a fluorescent calibration composition in which a pin is dipped to receive the composition for spotting.
Figure 11:
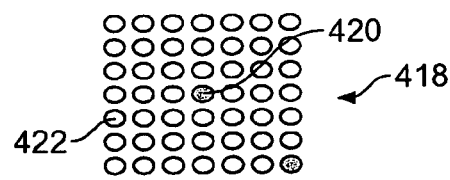
FIG. 11 shows diagrammatically a spotted microarray of biological spots among which is a pattern of fluorescent calibration spots produced with the composition of FIG. 10.

With reference back to FIG. 10, as a step in forming the array of FIG. 11 (as well as the arrays of FIGS. 22 and 23) pin 400, which may be one of a set of simultaneously actuatable pins of a commercially available spot printer, is dipped into reference composition 440 held, for example, within one of the wells 442 of a microwell plate also being used for printing the biomaterial array. Instead of bio-material, this particular well 400 holds a reference solution such as polyimide (Kapton) dissolved in a suitable solvent. Thus, a user-applied reference array is applied when spotting the array of biological material. (In other cases geometric reference spots or fiducials and intensity calibration spots may be applied during manufacture of the device, e.g. before or after applying the substrate layer.)

Figure 19:
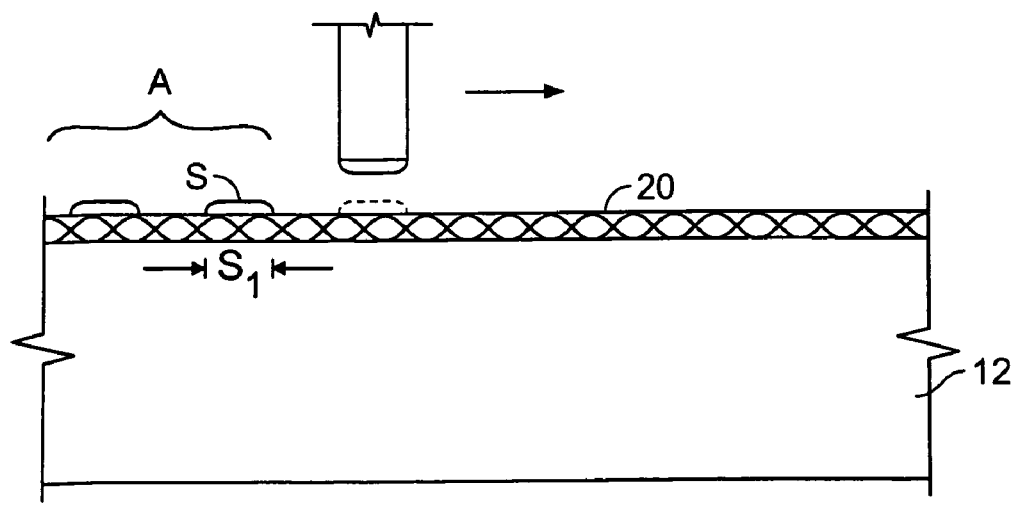
FIG. 19 illustrates diagrammatically spotting an array of biological material upon an ultra-thin bio-material-immobilizing polymeric substrate layer, produced as above, to be followed by performance of an assay that binds and fluorescently tags selected spots in the array, followed by washing and imaging.

FIGS. 10, 11 and 19 illustrate pin 400 contacting slide 100 to deposit composition 440 forming spot S. Typical diameters for spots 422 of biological material are 150 micron and 300 micron, and the same size spots may be used for the simultaneously-applied intensity calibration reference spots 420, using the previously mentioned synthetic resin material, such as a polyimide polymer (Kapton), which exhibits temporally stable broad fluorescence properties. By being presented in solution with a suitable volatile solvent and deposited as spots on the slide surface, evaporation leaves adherent fluorescence intensity calibration spots in a reference pattern interspersed with the more numerous spots 420 of bio-material. The same printer used to deposit the array 418 of biological material spots 422, may thus be used to deposit calibration spots 420 on the slide. The amount of material deposited for spots 420 is not critical since polymers such as Kapton are optically opaque, from which fluorescent emission 464 occurs at or near the surface, with the reproducible quantum yields.

The use of the calibration spots 420, however applied to each slide, enables instrument self-calibration. In fact, auto calibration of the instrument may be accomplished for each slide, using e.g. 6 calibration spots on a slide.

It is further found that non-uniformities of illumination of a microarray as may occur with the side lighting operating in dark field reflection mode can be accommodated with a dispersed pattern of intensity calibration spots such as shown in FIG. 23 to normalize the detected results.

Figure 21:
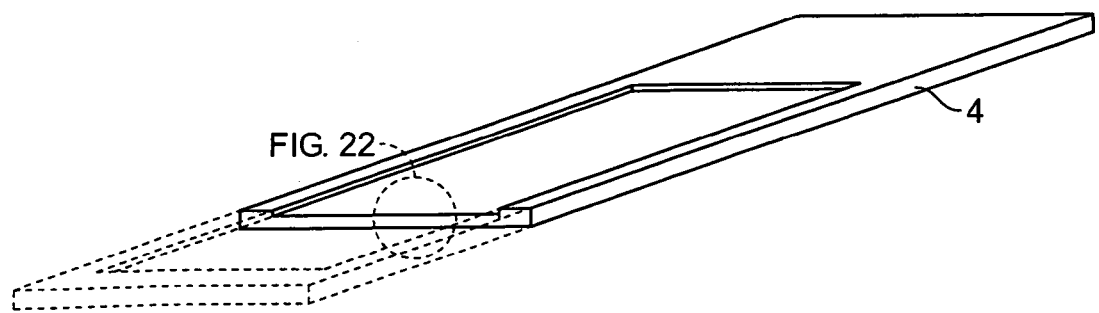
Figure 22:
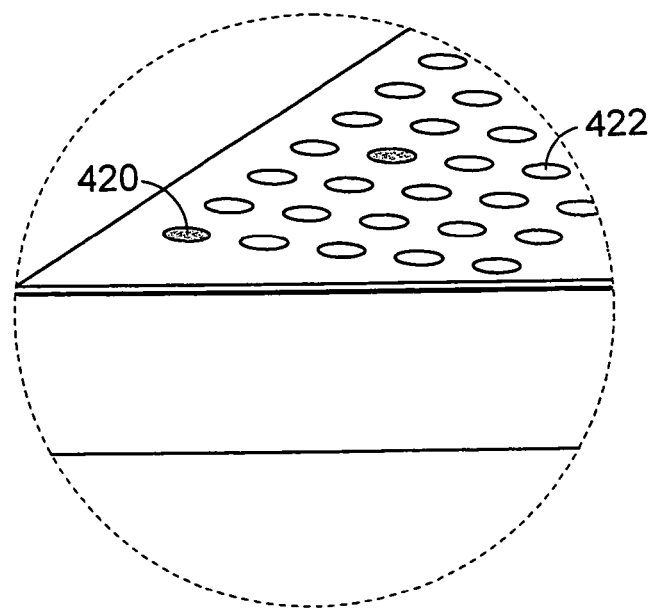
FIG. 22 is a magnified view of a portion of FIG. 21 showing, in addition to biological spots, fluorescent intensity calibration and fiducial calibration spots.

FIG. 21 shows a pre-spotted bio-cassette (cover not shown), having a protein-immobilizing substrate that may be offered to clinics, bearing a diagnostic protein array of spots 422 and intensity and/or registration calibration spots 420, see FIG. 22. The clinical laboratory may react a patient's fluid with the array to determine a disease condition.

Besides the planar rigid supports described, bio-immobilizing polymer may be applied to other surfaces such as by chemical vapor deposition upon the bottoms of wells of multi-well plates or to inside surfaces of hollow reaction tubes.

Referring to FIGS. 23 and 24A, a number of spotted micro arrays 418 are often placed upon the same microscope slide 10, intended to be reacted with different fluids, for different assays, for instance using extracts of blood from different subjects. To protect against cross-contamination, typically a fluid-tight elastomeric gasket 430, in the form of a grid of upstanding walls 432, is pressed tightly against the face of the microscope slide. This defines individual wells at individual arrays 418. Such an arrangement is shown in FIG. 24D, in which spotted arrays 418 are individually surrounded by walls 432 of the grid-form gasket 430 that is pressed tightly against the substrate layer 20" on the microscope slide surface.

Different aliquots of fluid are then introduced to the respective wells and reacted with the arrays of spots, following which the fluid may be extracted and the bottom of the wells washed.

For reading the arrays, the gasket is removed, and the microscope slide placed beneath a microscope, its field of view suggested by the circle in FIG. 24E. In the gasket removal step, the gasket sometimes adheres to the substrate layer more tenaciously than the substrate layer adheres to its support, and the substrate is lifted or disrupted. This can destroy readability of the micro arrays or introduce possibilities of error in their microscopic examination.

According to the invention, a substrate layer 20", e.g. of nitrocellulose or polystyrene, is applied to a rigid support 12, as in the previous embodiments with an intervening adhesion promoting layer 14' being first applied to the rigid support, but in this instance, a pattern of disruptions or moats M is formed in the substrate layer 20", such that each portion of substrate on which an array is located is isolated from the portions of the substrate layer upon which the gasket walls press. It is found that a substrate layer so formed prevents the micro arrays from being disrupted when the gasket is removed.

This segmentation may be achieved for instance by laser cutting or otherwise scoring a preformed continuous substrate layer to provide separation of the substrate of each array from adjoining substrate. In a presently preferred form, however, the moats M are formed during formation of the substrate by a simple and inexpensive technique. The adhesion promoting layer is applied with a pattern of interruptions corresponding to the desired location of the moats M. Where the adhesion promoting layer is a metal oxide layer, this may be accomplished by metallizing the surface of the rigid support, as by sputter coating, through a grid-form mask, define lines in which no adhesion promoter reaches the rigid support, or by laser etching after metallization. It is found that subsequent formation of the substrate layer by application of fluid, as by use of the drawing technique depicted in FIG. 14, produces the desired separation of the array portions of the substrate. Upon initial application of the fluid, the interruptions in the adhesion promoting layer occurs are covered by fluid, such as nitrocellulose or polystyrene in solution. But, as the fluid dries, the fluid is found to recede from the masked regions that have no surface adhesion promoter. This forms the desired isolating moats M in the substrate as shown in FIG. 24C. The moats may for instance have a width of 0.005 inch.

Figure 25B:
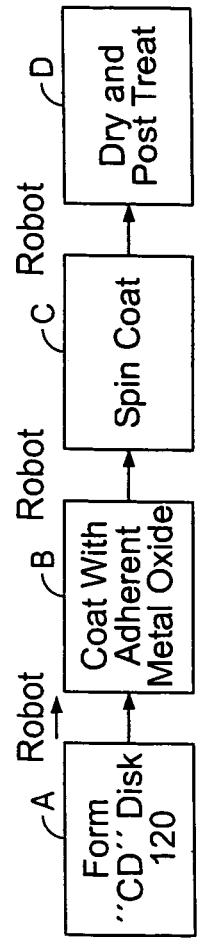
FIG. 25B is a block diagram of a forming sequence for forming a "CD" rigid support having an ultra-thin substrate coating of a bio-polymer-immobilizing polymer.
Figure 25:
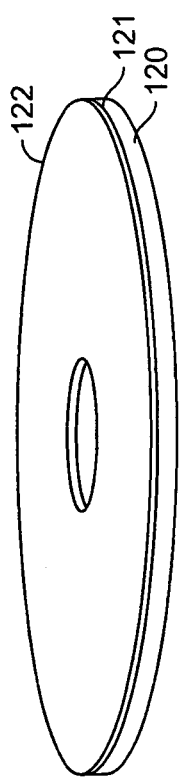
FIG. 25 is a diagrammatic perspective view of a "CD" shaped bio-cassette with over removed.
Figure 25A:
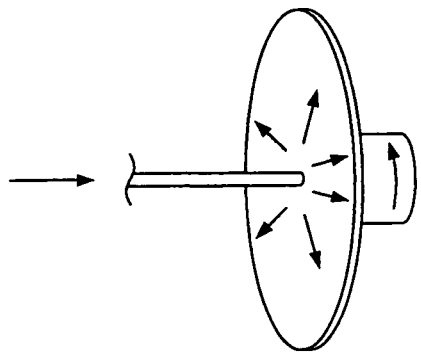
FIG. 25A is a diagrammatic perspective view of a "CD" spinner, illustrating spin coating of a single "CD"-shaped support.
Figures 27, 28:
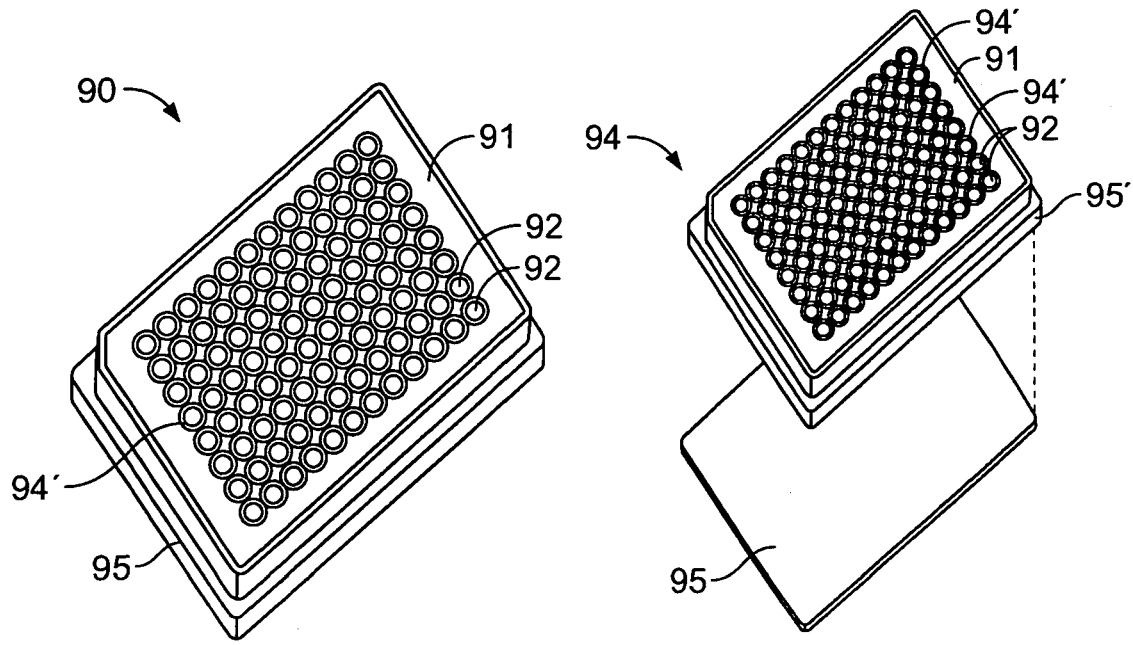
FIG. 27 is a perspective view of an assembled multi-well plate.
FIG. 28 is an exploded view of the multi-well plate of FIG. 27.
Figure 29:
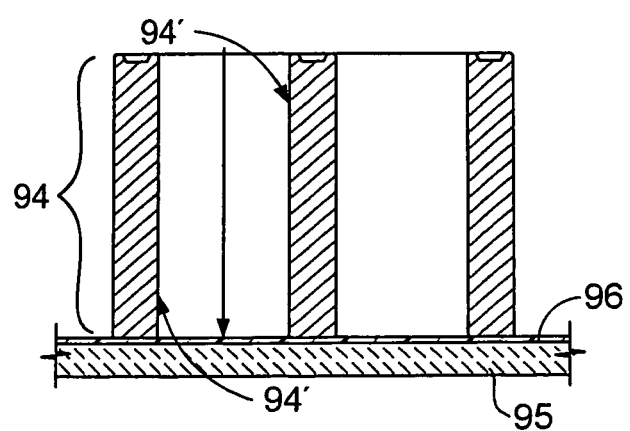
FIG. 29 is a vertical cross-sectional view of the assembly of FIG. 27.

Referring to FIGS. 25, 25A and 25B, another system for producing an ultra-thin bio-immobilizing product is provided. Round, thin "CD" type discs 120 of relatively rigid material are formed at station A. This base support structure may be of PMMA or polystyrene. Following this, using robots as developed in the industry, each automatically formed disc is introduced at station B to a vacuum chamber to receive a thin, adhesion promoting coating 121 of metal such as tantalum or aluminum, such as has been applied to semiconductor discs in the semiconductor industry. The coating is exposed to conditions forming an adherent oxide, e.g. tantalum oxide or aluminum oxide.

Following that, at station C, one-by-one, the automatically formed discs 120 with adhesion promoting coating 121 are introduced to a spin coating station, C, formed of standard spinning equipment, e.g. from the semi-conductor industry. A layer of coating solution is either applied prior to introduction to each disc, or, as shown, is applied, first at slow rotation speed at the spin coating station, to the center of the disc, the disc being supported and spun from beneath. Following this, the so-coated disc is spun at high speed, to remove from the surface of the disc all of the solution except that thin layer that is retained by the inherent adhesion forces existing between the fluid and the metal oxide coating. Either while still at station C, or preferably at station D, the applied layer is dried. At that station, or at a subsequent station, the formed layer may be subjected to a desired post-treatment, and then may be assembled with cover and other structure to complete a bio-cassette.

Figure 26:
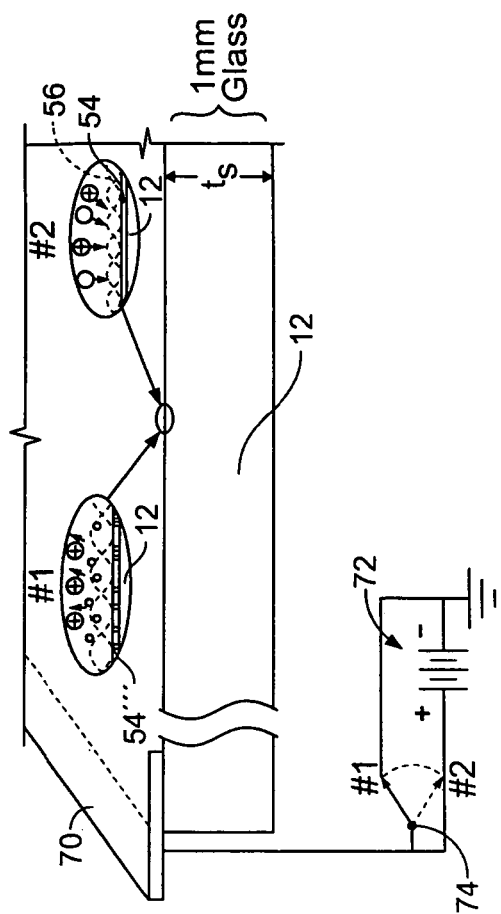
FIG. 26 illustrates the application of an electrical potential to a substrate and an effect that can be obtained.

The FIG. 26 diagram of a composite is intended as a general illustration, e.g. to illustrate the cross-section of a planar microscope slide, a bio-cassette, a disc-form substrate, the bottom of a micro-well plate or other useful configuration for presenting material on a substrate for microscopic examination from the substrate side.

A support 12, e.g. of glass of 1 mm thickness, has a surface to which a thin adherent metal oxide layer 54 has been applied, in the example, tantalum oxide, as before. To the outside surface of the adherent metal oxide layer 54 is applied a bio-compatible substrate 56, e.g. of nitrocellulose or polystyrene, which may advantageously be of the ultra-thin dimension described above or, depending upon imaging requirements, may be thicker. Subsequently the bio-material spots are applied.

In the embodiment of FIG. 26, novel advantage is taken of the electrically conductive properties of the adherent oxide coating. A terminal 70 is associated with conductive layer 54''' underlying the substrate 56, and connected to a battery 72 or other controllable potential source. As shown, a controller, 74, e.g. a switch and rheostat, has settings #1 and #2, typically more. As suggested in this diagram, at setting #2 a positive electrical potential is applied to conductive layer 54''' of a level to increase the binding affinity of a target molecule as well as an accompanying molecule of lesser charge. After binding from the parent medium, the potential level may be changed to lower level, not shown, as by use of the rheostat. The target molecule remains bound, but binding force is so reduced or eliminated with respect to the accompanying molecule that it is washed away or otherwise detached from the substrate. The potential may be changed from positive to negative, setting #1, for use in situations where a selected negative potential will repel undesired molecules while still retaining the target molecule.

Referring to FIGS. 27-34a, a multiwell plate 90 is comprised of a bottomless upper structure 91 and a planar bottom glass plate member 95. The upper structure 91 is of extruded form, e.g., of polystyrene. Within the periphery of structure 91, an array of wells 92 is formed by a nest of tubular walls 94'. Other such honeycomb-type structures can be employed.

As is well known in biotechnology, wells of multiwell plates are intended to receive aliquots of unknowns and reagents, and fluorophore tags are excited and read by transmission of excitation light from an objective to and transmission of fluorescent radiation from the wells, across the transparent bottom plate, to an objective of a detection system.

In the field, there has been difficulty in bonding such polystyrene upper structure to glass. In accordance with another aspect of the present invention, on the bottom plate of glass (or a plate of polymer material such as polycarbonate also adhesively incompatible with polystyrene), a layer of adherence-promoting material is applied. In one embodiment the layer is formed in a pattern which matches the pattern of the lower edges 94a of the bottom-less upper structure 94 of the micro-well plate to be assembled. In the embodiment shown in FIGS. 27-34a the layer is uniformly applied across the upper surface of bottom plate 95. In the case that metal oxide layer is employed as the layer, the oxide coating is selected to be so thin as not to substantially impair light transmission qualities of the bottom plate. The portion of the applied layer beneath the lower edges facilitates the manufacture of the composite well-plate, as it enables the upper structure to be of material (e.g. polystyrene) that is adhesively incompatible with the bottom plate (e.g. glass).

Figure 30:
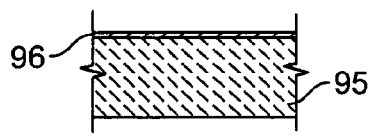
FIG. 30 is a magnified cross-sectional view of the bottom plate of the assembly of FIGS. 28 and 29.
Figure 31:
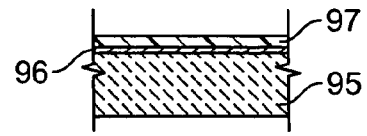
Figure 32:
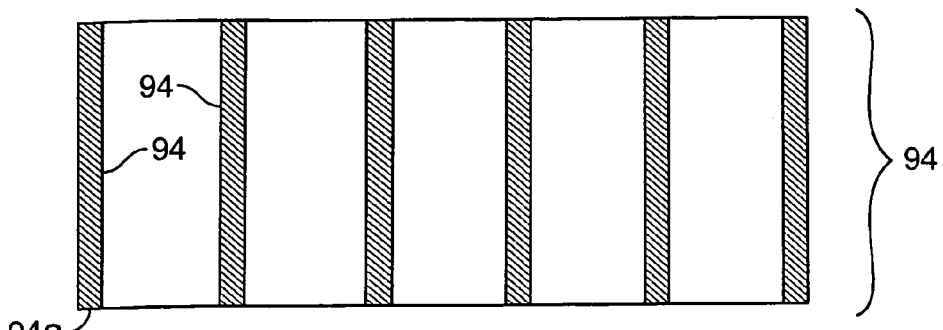
Figure 33:
Figure 34:
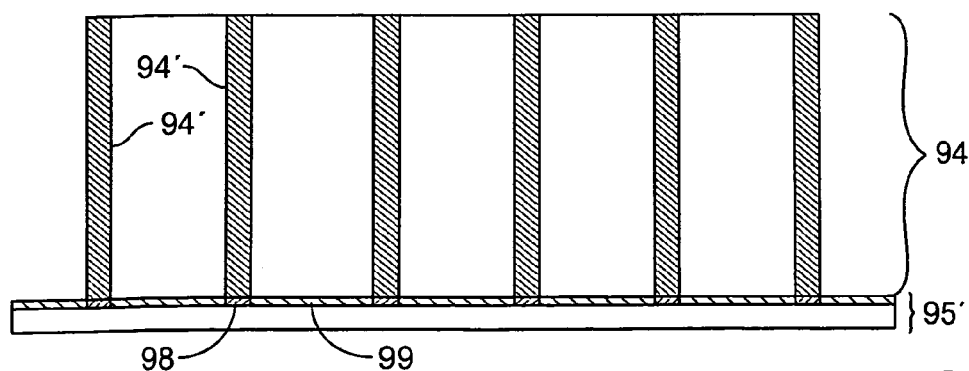
FIG. 34 is a similar view of the completed assembly and FIG. 34A is a view at increased magnification of a portion of the cross-section of FIG. 34.
Figure 34A:
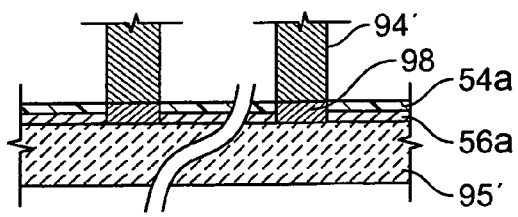

Referring to FIGS. 30 and 31, such an adhesively incompatible support plate 95, e.g. of glass for forming the bottom of a multi-well plate is uniformly coated with a film of an adhesion promoter 96, e.g. the tantalum oxide discussed, followed by application of a uniform upper film 97 of polystyrene or other substance that is adhesively compatible with the upper structure as well as suitable as a substrate for spots of bio-material. The bottomless upper elements of the micro-well plate may thus be of polystyrene and joined to a uniformly coated glass. The union may be enhanced by heat or by the temporary presence of a solvent such as Amyl Acetate or the temporary presence of a solution of polystyrene in such a solvent. The glass surface, coated with a thin film of polystyrene, may have its surface adhesion enhanced as described above, e.g. by corona treatment, to serve as a biomaterial receiving substrate at the bottom of the wells.

The uniform film of polystyrene coated over the adhesion promoter on the glass plate, may be an ultra-thin layer as previously described, and its areas within the grid of the multi-well plate may thus be suitable for receiving deposit of bio-molecules as previously discussed. Thus microscopic reading of the wells through the transparent bottom of the micro-well plate can be enhanced.

In the embodiment of FIGS. 32, 33, 34 and 34a, a pattern 98 of tantalum oxide or other suitable mutually adherent composition is applied to the plate 95', matching the geometry of the grid 94. In the spaces between those deposits a material is applied, e.g. a composite of an adhesive promotion layer 56a of any of those mentioned, and a bio-receiving substrate 54a of any of those mentioned, see FIG. 34A. For instance the composite may be an adherent oxide layer on the top of which a nitrocellulose or divinyl benzene substrate is applied.

For further disclosure concerning the topics of (1) employing the characteristics of ultra-thin substrate layers in dark field illumination and imaging on a solid state array of sensors of size of order of magnitude of the array of spots, in general and in particular of nitrocellulose and polystyrene, and their methods of manufacture and use, (2) metal oxide and other absorbent layers beneath the substrate that absorb excitation light serving to enhance the operation or make practical a clinical fluorescence reader and (3) formation and utilization of intensity calibration marks in microarrays for serving to enhance the operation of a fluorescence reader, in particular one using a high intensity light emitting diode or diode array for excitation illumination, reference is made to a further PCT application being filed simultaneously herewith, which likewise claims priority from U.S. Provisional Ser. No. 60/476,512, filed Jun. 6, 2003.

Other features and advantages of the invention will be understood from the foregoing and the claims and are within the spirit and scope of the invention.

What is claimed is:

1. A device constructed for immobilizing bio-material capable of being associated with a fluorophore tag or luminescent tag for optically-stimulated fluorescent emission analysis or for luminescence analysis, comprising a coating of nitrocellulose polymer of thickness less than 5 micron, the coating adhered to a rigid support via one or more adherent intervening layers comprising at least an adherent metal oxide intervening layer, the nitrocellulose coating having an outer deposit-receiving surface that has enhanced binding capability for the bio-material as the result of exposure of the coating surface to corona treatment, and a deposit of the bio-material immobilized on the corona-treated surface of the nitrocellulose coating.

2. The device of claim 1 in which the nitrocellulose coating is microporous.

3. The device of claim 1 in which the nitrocellulose coating is a solid film.

4. The device of claim 3 in which the solid film is less than 3 micron in thickness.

5. A device constructed for immobilizing a bio-material capable of being associated with a fluorophore tag or luminescent tag for optically-stimulated fluorescent emission analysis or for luminescence analysis, comprising a coating of nitrocellulose polymer of thickness less than 5 micron, the coating adhered to a rigid support via one or more adherent intervening layers, the nitrocellulose coating having an outer deposit-receiving surface that has enhanced binding capability for the bio-material as the result of exposure of the coating surface to an energetic surface-altering treatment, and a deposit of the bio-material immobilized on the treated nitrocellulose surface.

6. The device of claim 5 in which the treated surface of the nitrocellulose coating is the result of exposure of the surface to corona treatment.

7. The device of claim 5 in which the treated surface of the nitrocellulose coating is the result of exposure of the surface to charged particles.

8. The device of claim 5 in which the treated surface of the nitrocellulose coating is the result of exposure of the surface to gamma radiation.

9. The device of claim 5 in which the treated surface of the nitrocellulose coating is the result of exposure of the outer surface to at least one of corona treatment, flame treatment, bombardment by charged particles comprising electrons, ions or sub-atomic particles, or electromagnetic radiation of ultraviolet, gamma or X-ray wavelength.

10. The device of claim 1, 5 or 9 in which the nitrocellulose coating is a dried residue of a coating solution of nitrocellulose and a volatile solvent.

11. The device of claim 10 in which the nitrocellulose coating is the product resulting from the process of immersing the rigid support in a bath of the coating solution and progressively drawing the rigid support from the bath under conditions in which the solvent evaporates during the drawing.

12. The device of claim 5 or 9 in which said intervening layer is comprised of an adherent metal oxide or a silicon-based material.

13. The device of claim 1, 5 or 9 in which said intervening layer is comprised of tantalum oxide.

14. The device of claim 5 or 9 in which said intervening layer is comprised of silane.

15. The device of claim 5 or 9 in which the rigid support is of glass and said adherent intervening layer is comprised of silane, epoxy silane, polylisine, PEI, GAP, an adherent metal oxide, colloidal silica or a soluble silicate.

16. The device of claim 1, 5 or 9 in which the rigid support is substantially transparent and a said intervening layer is substantially opaque.

17. The device of claim 6 in which the substantially opaque intervening layer is comprised of tantalum oxide.

18. The device of claim 1, 5 or 9 in which the outer surface of the nitrocellulose coating and the immobilized bio-material thereon is arranged to be exposed from the exterior for optical stimulation of a fluorophore tag associated with the bio-material and analysis of resultant emission from the fluorophore tag, the rigid support being substantially transparent and the one or more intervening layers being collectively sufficiently opaque to substantially block, from entering the rigid support, radiation of wavelengths corresponding to the stimulating and emission wavelengths of the fluorophore tag associated with the immobilized bio-material.

19. The device of claim 1, 5 or 9 in which the rigid support, the one or more intervening layers and the nitrocellulose coating collectively are functionally transparent to light to enable optical excitation of a fluorophore taa asociated with the deposit of bio-material on said coating by excitation radiation passing through said rigid support, or to enable microscopic analysis through said rigid support of optically-stimulated fluorescent emissions passing from a fluorophore tag associated with the deposit of bio-material on said coating, or to enable both.

20. The device of claim 19 in which a said intervening layer is functionally transparent silane or functionally transparent tantalum oxide.

21. The device of claim 5 or 9 in which an intervening layer is a coating comprising the product resulting from the process of immersing the rigid support in a bath of a coating solution comprising the material of the intervening layer and a solvent and progressively drawing the rigid support from the bath under conditions in which the solvent evaporates during the drawing.

22. The device of claim 1, 5 or 9 in which the outer surface of the nitrocellulose coating on the rigid support is generally flat, arranged to receive deposit of a spotted array of the bio-material.

23. The device of claim 22, including an array of spots of bio-material deposited on the nitrocellulose coating.

24. The device of claim 23 in which the array of spots of bio-material comprises protein, peptides, antibodies, viruses, or nucleic acid or other genetic material, receptors, eDNA clones, DNA probes, oligonucleotides including synthetic oligonuceleotides, or polymerase chain reaction (PCR) products, or plant, animal, human, fungal or bacterial cells, or malignant cells or cells from biopsy tissue.

25. The device of claim 1, 5 or 9 wherein the rigid support is in the form of a microscope slide.

26. The device of claim 5 or 9 comprising a coating of nitrocellulose of thickness less than about 3 micron, the rigid support comprising glass, the nitrocellulose coating being adhered to the rigid glass support via an intervening layer comprised of tantalum oxide or silane.

27. The device of claim 26 in which the nitrocellulose coating is a substantially solid film.

28. The device of claim 26 in which the nitrocellulose coating is the product resulting from the process of immersing the rigid support in a bath of a coating solution of nitrocellulose and a solvent and progressively drawing the rigid support from the bath under conditions in which the solvent evaporates during the drawing.

29. A device constructed for immobilizing a bio-material capable of becoming associated with a fluorophore tag or luminescent tag for optical emission analysis, comprising a coating of a polymer capable of binding with the bio-material, the coating having a thickness less than about 5 micron, the coating of polymer adhered to a rigid support via one or more adherent intervening layers, the coating of polymer having an outer deposit-receiving surface that has enhanced binding capability for the bio-material as the result of exposure of the surface to an energetic surface-altering treatment, and a deposit of the bio-material immobilized on the treated surface of the polymer coating.

30. The device of claim 29 in which the polymer is selected to immobilize protein material or cellular bio-material and the deposit on the coating is comprised of the respective material.

31. The device of claim 29 in which the treated surface is the result of exposure of the outer surface of the polymer coating to corona treatment.

32. The device of claim 29 in which the treated surface is the result of exposure of the outer surface of the polymer coating to at least one of corona treatment, flame treatment, bombardment by charged particles comprising electrons, ions or sub-atomic particles, or electromagnetic radiation of ultraviolet, gamma or X-ray wavelength.

33. The device of claim 29, 31 or 32 in which a said intervening adherent layer between the coating of polymer and the rigid support is comprised of tantalum oxide or silane.

34. The device of claim 29, 31 or 32 in which the rigid support is of glass and said intervening adherent layer between the coating of polymer and the rigid support is comprised of silane, epoxy silane, polylisine, PEI, GAP, an adherent metal oxide, colloidal silica or a soluble silicate.

35. The device of claim 29, 31 or 32 in which the polymer coating is a dried residue of a coating solution of the polymer and a solvent.

36. The device of claim 35 in which the polymer coating is the product resulting from the process of immersing the rigid support in a bath of the coating solution and progressively drawing the rigid support from the bath under conditions in which the solvent evaporates during the drawing.

37. The device of claim 29, 31 or 32 in which the polymer coating is of thickness less than three micron.

38. The device of claim 29, 31 or 32 in which the coating of polymer is nitrocellulose or polystyrene.

39. The device of claim 29, 31 or 32 in which the outer surface of the coating of polymer on the rigid support is generally flat, arranged to receive deposit of a spotted array of bio-material.

40. The device of claim 39 including an array of spots of bio-material deposited on the layer.

41. The device of claim 40 in which the array of deposited spots of bio-material comprises protein, peptides, antibodies, viruses, or nucleic acid or other genetic material, receptors, cDNA clones, DNA probes, oligonucleotides including synthetic oligonuceleotides, or polymerase chain reaction (PCR) products, or plant, animal, human, fungal or bacterial cells, or malignant cells or cells from biopsy tissue or other bio-material.

42. The device of claim 29, 31 or 32 wherein the rigid support is in the form of a microscope slide.

43. The device of claim 29, 31 or 32 in which the outer surface of the coating of polymer and the immobilized bio-material thereon are arranged to be exposed from the exterior for optical stimulation of a fluorophore tag associated with the bio-material and analysis, the rigid support being substantially transparent and the one or more intervening layers being collectively sufficiently opaque to substantially block light from the rigid support.

44. The device of claim 43 in which the intervening layer is comprised of a substantially opaque layer of tantalum oxide.

45. The device of claim 29, 31 or 32 in which the rigid support, the one or more intervening layers, and the coating of polymer are collectively functionally transparent to light to enable optical excitation of a fluorophore tag associated with the deposit of bio-material on said coating by excitation radiation passing through said rigid support, or to enable microscopic analysis through said rigid support of emissions from a fluorophore tag or luminescent tag associated with the deposit of bio-material on said coating, or to enable both.

46. The device of claim 45 in which a said intervening layer is functionally transparent silane or functionally transparent tantalum oxide.

47. A method of forming the device of claims 1, 5 or 29, comprising providing the rigid support with the one or more adherent intervening layers and forming thereon the polymer coating.

48. The method of claim 47 in which the coating is formed by applying a coating solution of the polymer and a volatile solvent to an adherent intervening layer on the rigid support, and evaporating the solvent to form the coating layer as a dried residue of the polymer.

49. The method of claim 48 in which the coating is applied to the support by immersing the rigid support in a bath of the coating solution and progressively drawing the support from the bath of the coating solution under conditions in which the solvent evaporates during the drawing.

50. The method of claim 47 followed by subjecting the exposed surface of the coating to an energetic surface-altering treatment to enhance the binding capability of the coating for the bio-material.

51. The method of claim 50 in which the treatment is corona treatment, flame treatment, bombardment by charged particles comprising electrons, ions or sub-atomic particles, or electromagnetic radiation of ultraviolet, gamma or X-ray wavelength.

52. A method of emission analysis comprising providing the device of claim 1, 5 or 29, including applying said bio-material as an array of spots of material to the outer deposit-receiving surface of the polymer coating, conducting an assay which tags at least some of the spots with a fluorescent or luminescent label, and, after washing the array, reading the array by optical detection.

53. The method of claim 52 in which reading is accomplished by a CCD sensor.

54. The device of claim 29 constructed for immobilizing bio-material in the form of protein bio-material or cellular bio-material, wherein the coating is comprised of nitrocellulose polymer or polystyrene polymer that is ultra-thin, having a thickness $t_{ut}$ less than about 3 micron, the treated surface is the result of exposure of the outer surface of the polymer coating to at least one of corona treatment, flame treatment, bombardment by charged particles comprising electrons, ions or sub-atomic particles, or electromagnetic radiation of ultraviolet, gamma or X-ray wavelength, and the coating carrying a deposit of protein bio-material or cellular bio-material.

55. The device of claim 54 wherein said coating is a substantially transparent solid film.

56. The device of claim 1, 29 or 54 wherein an array of spotted deposits of the bio-material is disposed on the deposit-receiving surface for use in the performance of an assay.

57. The device of claim 54 or 55 in which the coating is a dried residue of a coating solution of nitrocellulose or polystyrene and a volatile solvent.

58. The device of claim 57 wherein the coating is the product resulting from the process of immersing the rigid support in a bath of the coating solution and progressively drawing the rigid support from the bath under conditions in which the solvent evaporates during the drawing.

59. The device of claim 54 or 55 wherein the deposit-receiving surface of said coating is in a corona-treated state.

60. The device of claim 54 or 55 wherein the deposit-receiving surface of said substrate layer is in a treated state produced by an energetic surface-altering treatment comprising exposure of the outer surface to electromagnetic radiation of gamma wavelength.

61. The device of claims 54 or 55 wherein a said intervening layer is of substance selected from the group consisting of silane. epoxy silane, polylisine, PEI, GAP, an adherent metal oxide, colloidal silica and soluble silicates.

62. The device of claim 61, wherein a said intervening layer is silane.

63. The device of claim 61, wherein a said intervening layer is tantalum oxide.

64. The device of claim 61, wherein the rigid support has characteristic luminescence or fluorescence in response to incident stimulating radiation, a said intervening layer being sufficiently opaque to be effective to at least substantially limit passage of light between the rigid support and the coating of polymer.

65. The device of claim 54 or 55 in which the coating has thickness less than about 1 micron.

66. The device of claim 65 in which the coating is a substantially solid, substantially transparent film of thickness $t_{uts}$ between about 0.1 and 0.5 micron.

67. The device of claim 65 in which the coating of polymer is polystyrene.

68. A device constructed for immobilizing bio-material capable of becoming associated with a fluorophore tag or luminescent tag for optical emission analysis, comprising a deposit-receiving coating of substantially solid nitrocellulose of thickness less than 5 micron adhered to a rigid support via one or more adherent intervening layers at least one of which is an adherent metal oxide, the adherent intervening layer, or layers collectively being substantially opaque, the coating of nitrocellulose having an outer deposit-receiving surface in corona-treated state for enhanced immobilization of the bio-material and a deposit of the bio-material immobilized on the corona-treated nitrocellulose deposit-receiving surface.

69. A device constructed for immobilizing bio-material capable of becoming associated with a fluorophore tag or luminescent tag for optical emission analysis, comprising a deposit-receiving coating of substantially solid nitrocellulose of thickness less than 5 micron adhered to a rigid support via one or more adherent intervening layers at least one of which is an adherent metal oxide, the adherent intervening layer, or layers collectively, being substantially opaque, the coating of nitrocellulose having an outer deposit-receiving surface in surface-treated state for enhanced immobilization of the bio-material, the surface-treated state being the result of exposure of the outer surface of the coating of nitrocellulose to at least one of corona treatment, flame treatment, bombardment by charged particles comprising electrons, ions or sub-atomic particles, or by electromagnetic radiation of ultraviolet, gamma or X-ray wavelength, and a deposit of the bio-material immobilized on the surface-treated nitrocellulose deposit-receiving surface.

70. A device constructed for immobilizing bio-material capable of becoming associated with a fluorophore tag or luminescent tag for optical emission analysis, comprising a deposit-receiving coating of substantially solid nitrocellulose of thickness less than 5 micron adhered to a rigid support via one or more adherent intervening layers, the coating of nitrocellulose having an outer deposit-receiving surface in treated state for enhanced immobilization of the bio-material, the surface-treated state being the result of exposure of the outer surface to at least one of corona treatment, flame treatment, bombardment by charged particles comprising electrons, ions or sub-atomic particles, or electromagnetic radiation of ultraviolet, gamma or X-ray wavelength, and a deposit of the bio-material immobilized on the surface-treated nitrocellulose deposit-receiving surface.

* * * * *

UNITED STATES PATENT AND TRADEMARK OFFICE
CERTIFICATE OF CORRECTION

PATENT NO.        : 7,384,742 B2
APPLICATION NO. : 10/524614
DATED             : June 10, 2008
INVENTOR(S)       : Jean I. Montagu, Roger Dowd and David Root It is certified that error appears in the above-identified patent and that said Letters Patent is hereby corrected as shown below:

On the Title page item [54] (title), Column 1, Line 1; replace:
"ISOLATING" with
-- ISOLATING, --

On the Title page item [57] (abstract), Column 2, Line 19; replace:
"equipment" with
-- equipment. --

On Page 1, Specification, Column 1, Line 1; replace:
"ISOLATING" with
-- ISOLATING, --

Column 32, Line 65 at Claim 19; replace:
"taa" with
-- tag --, therefore.

Column 33, Line 24 at Claim 24; replace:
"eDNA" with
-- cDNA --.

Column 33, Line 25 at Claim 24; replace:
"Oligonuceleotides," with
-- oligonucleotides, --

Column 34, Line 32 (approx.) at Claim 42; replace:
"oligonuceleotides," with
-- oligonucleotides --, therefore.

Column 34, Line 62 (approx.) at Claim 47; replace:
"claims" with
-- claim --, therefore.

Column 35, Line 60 at Claim 61; replace:
"claims" with
-- claim --, therefore.

UNITED STATES PATENT AND TRADEMARK OFFICE
CERTIFICATE OF CORRECTION

PATENT NO.       : 7,384,742 B2
APPLICATION NO.  : 10/524614
DATED            : June 10, 2008
INVENTOR(S)      : Jean I. Montagu, Roger Dowd and David Root It is certified that error appears in the above-identified patent and that said Letters Patent is hereby corrected as shown below:

Column 35, Line 62 at Claim 61; replace:
"silane." with
-- silane, --, therefore.

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,384,742 B2 Page 1 of 1
APPLICATION NO. : 10/524614
DATED : June 10, 2008
INVENTOR(S) : Jean I Montagu et al.

It is certified that error appears in the above-identified patent and that said Letters Patent is hereby corrected as shown below:

Title Page

On title page, item 60 Related US Application Data, please add:

Provisional Application No. 60/404,237, filed on August 16, 2002; Provisional Application No. 60/430,299, filed on December 2, 2002; Provisional Application No. 60/476,512, filed on June 6, 2003.

Signed and Sealed this

Twenty-second Day of June, 2010

David J. Kappos
*Director of the United States Patent and Trademark Office*